United States Patent
Dewaele et al.

(10) Patent No.: US 10,962,093 B2
(45) Date of Patent: Mar. 30, 2021

(54) TORQUE-TRANSMITTING STEERING MECHANISM FOR A STEERABLE TOOL

(71) Applicant: STEERABLE INSTRUMENTS NV, Sint-Denijs-Westrem (BE)

(72) Inventors: Frank Dewaele, De Pinte (BE); Cyriel Mabilde, Oudenaarde (BE); Bart Blanckaert, Eeklo (BE); Alain Kalmar, Ghent (BE); Lieven Maene, Knokke (BE)

(73) Assignee: STEERABLE INSTRUMENTS NV, Sint-Denijs-Westrem (BE)

( * ) Notice: Subject to any disclaimer, the term of this patent is extended or adjusted under 35 U.S.C. 154(b) by 634 days.

(21) Appl. No.: 15/502,002

(22) PCT Filed: Aug. 27, 2015

(86) PCT No.: PCT/EP2015/069628
§ 371 (c)(1),
(2) Date: Feb. 6, 2017

(87) PCT Pub. No.: WO2016/030457
PCT Pub. Date: Mar. 3, 2016

(65) Prior Publication Data
US 2017/0234411 A1 Aug. 17, 2017

(30) Foreign Application Priority Data
Aug. 27, 2014 (EP) ..................... 14182381

(51) Int. Cl.
*A61B 1/008* (2006.01)
*F16H 19/00* (2006.01)
(Continued)

(52) U.S. Cl.
CPC ..... *F16H 19/005* (2013.01); *A61B 17/00234* (2013.01); *A61B 17/29* (2013.01);
(Continued)

(58) Field of Classification Search
CPC ............. A61B 34/71; A61B 2034/306; A61B 2034/301; A61B 1/0057; A61B 17/3421;
(Continued)

(56) References Cited

U.S. PATENT DOCUMENTS 5,114,402 A * 5/1992 McCoy ................ A61B 1/0051
600/143
7,410,483 B2 * 8/2008 Danitz ................ A61B 1/0055
606/1
(Continued)

FOREIGN PATENT DOCUMENTS

WO 2007/139734 A2 12/2007

OTHER PUBLICATIONS

International Search Report dated Oct. 21, 2015 for PCT/EP2015/069628.
(Continued)

*Primary Examiner* — Randell J Krug
(74) *Attorney, Agent, or Firm* — Amster, Rothstein & Ebenstein LLP

(57) ABSTRACT

Disclosed is a steerable tool with proximal and distal ends comprising a mechanical transmission system (MTS), shaft region, omnidirectionally moveable bendable proximal part (BPP), and omnidirectionally moveable bendable distal part responsive to movement of the BPP, where the MTS comprises longitudinal members (LM) each having proximal and distal ends, arranged in a longitudinal direction around a fictive tube, and has a corresponding transmission shaft region (TSR), transmission bendable proximal part (TBPP) and transmission bendable distal part (TBDP), wherein a plane section of at least one LM has an anisotropic area moment of inertia, and the majority of the LMs are axially rotationally constrained at one or more constraining points along the TBDP or TSR, the LMs are longitudinally slidable
(Continued)

with respect to each constraining point, and the MTS is configured such that the TBDP tip is axially rotatable in a bent position by a complementary rotation of the TBPP.

17 Claims, 8 Drawing Sheets

(51) Int. Cl.

| | | |
|---|---|---|
| *A61B 34/00* | (2016.01) | |
| *A61B 17/29* | (2006.01) | |
| *A61B 34/35* | (2016.01) | |
| *A61B 17/00* | (2006.01) | |
| *A61M 25/01* | (2006.01) | |
| *B25J 9/06* | (2006.01) | |
| *A61B 34/30* | (2016.01) | |
| *A61B 17/34* | (2006.01) | |
| *A61B 1/005* | (2006.01) | |

(52) U.S. Cl.
CPC ............ *A61B 34/35* (2016.02); *A61B 34/70* (2016.02); *A61B 34/71* (2016.02); *A61M 25/0138* (2013.01); *A61M 25/0147* (2013.01); *B25J 9/06* (2013.01); *A61B 1/0057* (2013.01); *A61B 17/3421* (2013.01); *A61B 2017/00314* (2013.01); *A61B 2017/00323* (2013.01); *A61B 2017/291* (2013.01); *A61B 2034/306* (2016.02)

(58) Field of Classification Search
CPC .... A61B 2017/291; A61B 2017/00305; A61B 2017/00313; A61B 2017/00323
See application file for complete search history.

(56) References Cited

U.S. PATENT DOCUMENTS

| | | |
|---|---|---|
| 2003/0018323 A1 | 1/2003 | Wallace et al. |
| 2003/0114832 A1 | 6/2003 | Kohler et al. |
| 2004/0162547 A1 | 8/2004 | Wallace et al. |
| 2006/0106288 A1* | 5/2006 | Roth .................. A61B 17/0218 600/204 |
| 2007/0038230 A1 | 2/2007 | Stone et al. |
| 2007/0156119 A1 | 7/2007 | Wallace et al. |
| 2008/0221393 A1 | 9/2008 | Padget et al. |
| 2008/0300462 A1 | 12/2008 | Intocccia et al. |
| 2010/0160736 A1 | 6/2010 | Padget et al. |
| 2011/0004157 A1 | 1/2011 | Dewaele et al. |
| 2013/0253481 A1 | 9/2013 | Dewaele et al. |
| 2014/0052061 A1 | 2/2014 | Weisshaupt et al. |
| 2017/0007224 A1* | 1/2017 | Sholev ................ A61B 1/0055 |

OTHER PUBLICATIONS

Written Opinion of the International Searching Authority dated Oct. 21, 2015 for PCT/EP2015/069628.

* cited by examiner

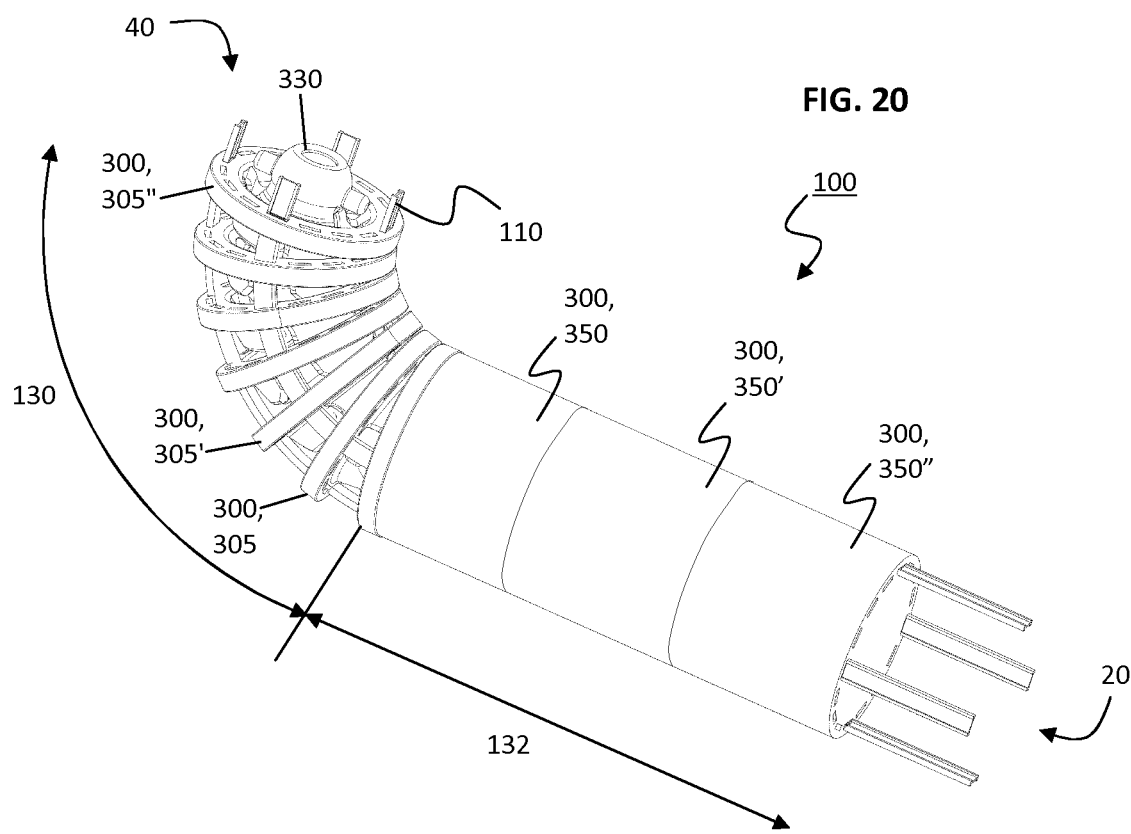
FIG. 20
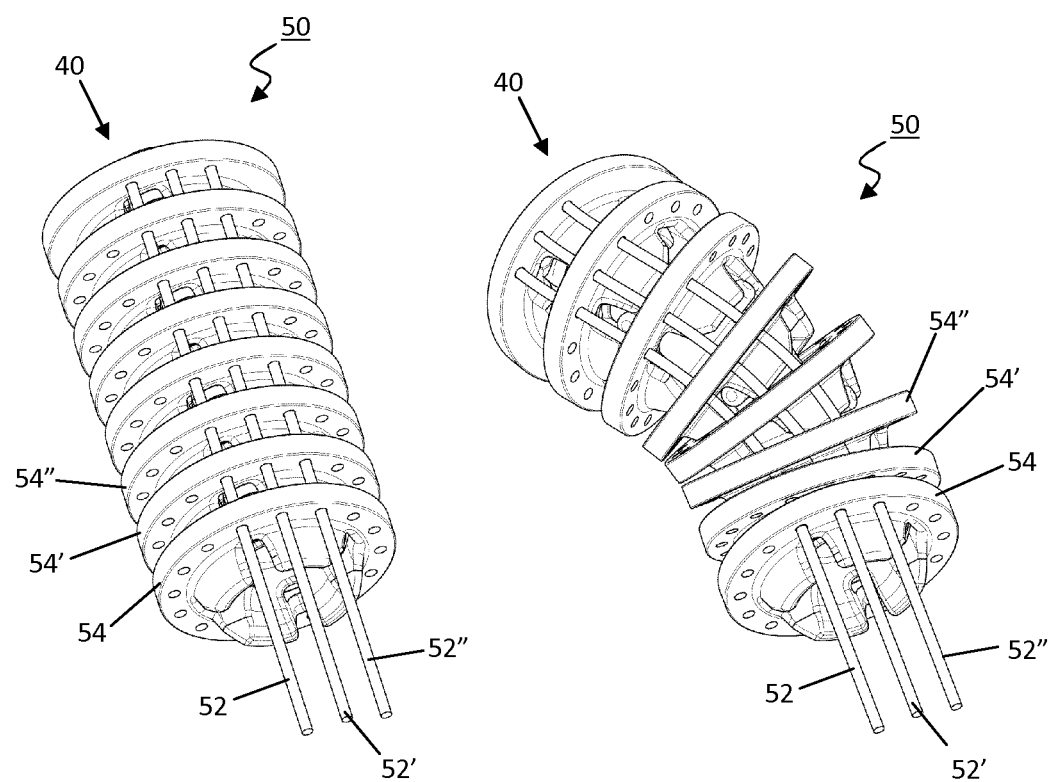
FIG. 21A
FIG. 21B

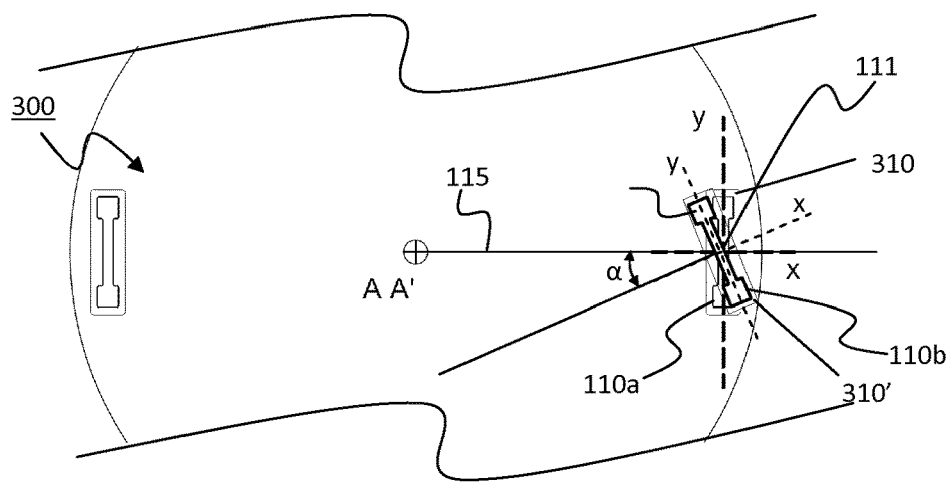
FIG. 22
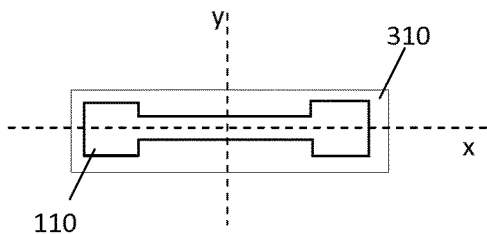
FIG. 22A
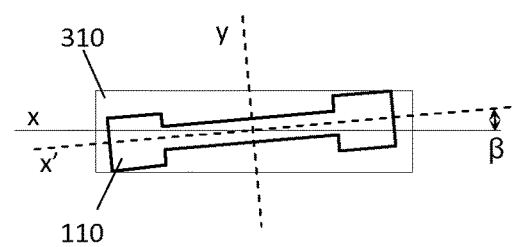
FIG. 22B
FIG. 23
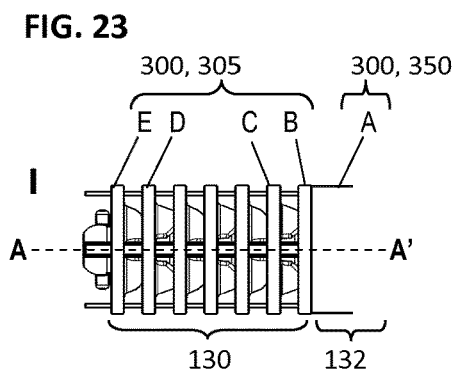
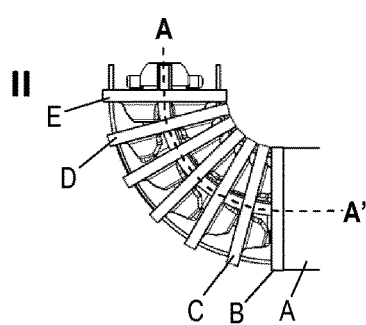
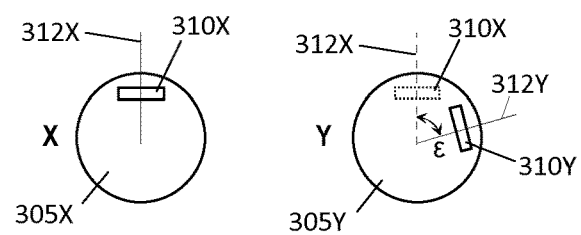
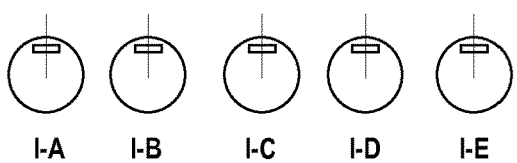
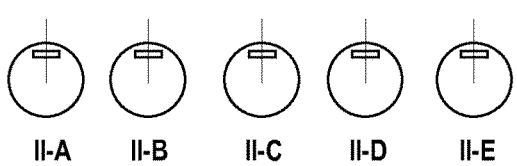

TORQUE-TRANSMITTING STEERING MECHANISM FOR A STEERABLE TOOL

CROSS-REFERENCE TO RELATED APPLICATIONS

This application is a U.S. national stage entry under 35 U.S.C. § 371 of PCT International Patent Application No. PCT/EP2015/069628, filed on Aug. 27, 2015, which claims priority to European Application No. 14182381.5, filed on Aug. 27, 2014, the contents of which are incorporated herein by reference in their entirety.

BACKGROUND TO THE INVENTION

Since the 1980s, open surgery has been largely replaced by an endoscopic approach, whereby long-shaft instruments are inserted through trocars in a gas-extended abdomen. Such laparoscopic surgery, known for its validated benefits of shorter hospitalization times, less post-operative pain, and earlier recovery, is more demanding for the surgeon.

A disadvantage of endoscopic surgery is reduced dexterity. This is mainly because of the fulcrum effect and the absence of wrist like movements at the tip of the instrument. Awareness of this disadvantage increases as more complex endoscopic procedures and single-port surgeries, characterised by "sword fighting" of the instruments, are performed.

The fulcrum effect involves pivoting of the long-shaft instruments at the level of the trocar (pivot point) inserted in the abdomen. A movement of the handle to the left is translated as a movement to the right at the effector (e.g. a pair of scissors), and vice versa. Surgeons are able to quickly adapt to these inverted movements.

The lack of wrist-like movements is more difficult to overcome. A state-of-the-art solution is provided by the Da Vinci robot (Intuitive Surgical) where movements of the surgeons' hands at the console are transferred to fluent movements at the instruments' tip. This solution is expensive, leading to the development of cheaper hand instruments with an omni-directional articulated tip.

Much of the surgical challenge is attributable to the reduced dexterity. A conventional rigid laparoscopic instrument offers only 4 degrees of freedom (rotation, up/down angulations, left/right angulations, in/out movements). To overcome this restriction in movements, various designs for steerable instruments have been developed:

1. In its simplest form, an articulated instrument comprises a pre-bent flexible tube, that is slidably unsheathed from a rigid straight tube. This tip can only bend in one direction (uni-directional articulated instrument) and can only withstand a limited amount of lateral force.

2. More advanced alternatives are instruments that allow bending movements of the tip in one plane e.g. left to right and vice versa. Because of the nature of the construction, a mostly stable tip is created. These bi-directional instruments need to be navigated to a point of interest by bending into one direction and then by turning the whole instrument around its own axis. This lacks intuitiveness.

3. True wrist movements are only possible with omni-directional systems. The omnidirectional articulated instrument consists mainly of a proximal and distal end, a distal bending part, a shaft region extending from the distal bending part, and optionally a proximal bending part. Movement of the proximal end is transferred to a movement at the distal end. Examples are described in U.S. Pat. No. 7,410,483 (FIG. 11), and U.S. Pat. No. 8,105,350 (FIG. 15).

Akin to robotic surgery, omni-directional articulated instruments provide up to 7 degrees of freedom (axial rotation and deflection of the tip in two planes are added to the 4 DOF of conventional rigid instruments). A combination of up/down and left/right movements at the proximal side allows any point at the distal effector side to be reached without the need for a rotation around its own axis. The increased maneuverability, however, is at the price of a significant decrease in tip stability. To solve this, hybrid solutions such as the Kymerax® system (Terumo) and Jaimy® system (EndoControl) compensate by using powerful electrical servo motors to restore the tip stability.

Omni-directional articulated instruments offer, in comparison to robotic systems, the advantages of low costs and tactile feedback.

The wrist of a surgical articulated instrument must be stable i.e. exhibit sufficient resistance the application of external forces. It has recently been studied by Chang Wook Jeong (Chang et al. Insufficient Joint Forces of First Generation Articulating Instruments for Laparoendoscopic Single-Site Surgery, Surgical Innovation 2012). He calculated that the instruments' wrist ideally withstands a minimal lateral force of 20N to be useful.

This stability can be achieved by increasing the instruments' diameter, increasing the number, section of the steering wires, reducing the length of the wrist or by using stiffer material. However, where the desire for reduced invasiveness requires a minimised diameter, comprises are needed with existing technologies.

In surgery, perhaps the most important feature is rotational stability. The ability to transmit rotary motion from the shaft over the instruments' wrist to the end effector. For instance, the movement of throwing a suture in backhand cutting position requires an instrument that is bent over about 70° and still allows a rotary movement of the needle holder to protrude tissues with the round needle.

A surgical instrument is considered omni-directional if using the orientation of the shaft as a reference, the bendable distal end part can move freely within a full cone angle. Typically a ball and socket joint is used. This is a 3 DOF joint that allows movements such as pitch (up-down), roll (left-right) and yaw (rotation). In order to allow rotary motion to be transmitted the rotational movement in the joint is ideally be constrained, for instance, using a pin and groove. An arcuate groove is provided in the socket and extends in a plane passing generally through the center of the ball and receives a pin which it is pivotally connected to the adjacent side of the ball. Another way is the use of a faceted ball and socket. The facets and edges block the axial rotation, however they reduce the angulation of some lateral orientations.

There are numerous ways in which a concatenation of revolute joints can be assembled to mimic the behaviour of a ball and socket joint. For instance, a universal joint is like a ball and socket joint, except it is constrained by one degree of rotational freedom. Two fork axes are joined together by a cross, the cross maintains these axes at 90 degrees, so if torque is applied to axis 1, axis 2 will rotate. A universal joint is equivalent to a hinge-2 joint where the hinge-2's axes are perpendicular to each other, and with a perfectly rigid connection in place. In articulated surgical instruments or articulated endovascular catheters, a universal joint is often achieved by a concatenation of flexible hinges that are oriented 90° to each other.

Omni-direction movement can be achieved using a kinematic chain that is an assembly of tandemly arranged links. A link is a rigid body which possesses points for attachment to other links. In human physiology, links can be seen as discs, vertebrae, or bones. A joint is a connection between links. A kinematic pair is a combination of two links with a joint in between. A kinematic chain is an assembly of links and joints. The instruments' wrist is the kinematic chain between shaft and end effector.

An interesting observation is that although the rotational freedom between two links is constrained, a kinematic chain containing such links can be forced into a configuration so that first and last links are rotated in respect of each other. When as all links and joints remain on one line, the rotary motion is transmitted without slack, and the first and last link maintain the same orientation. However, when the kinematic chain follows a spiral path a significant rotation between first and last link may occur. Omni-directional instruments based on a concatenation of (flexible) revolute joints are also prone to this phenomenon. In the case of surgical instruments this results in a rotation between shaft and end bendable distal part. In surgery this loss of revolute transmission is highly undesirable.

One solution in the art to reduce the 'spiral kinematic chain effect' is to reduce the number of links. US 2012/0220831 describes a multi-disc wrist joint with only 5 links and 4 joints. They claim that the tool has no singularity in roll, pitch or yaw. So the movements are smooth. This is true for robotic applications where every joint can be controlled individually. Additionally, corrections are easily made by means of appropriate inverse kinematics implemented in the computer controller. Using hand controlled instruments, the joints are hard to control especially if individual joints need to bent over 45°. They become 'notchy' and difficult to turn when operated at extreme angles.

The aim of the present invention is to provide a mechanical transmission system for a steerable instrument that overcomes one or more of the problems in the prior art.

SOME EMBODIMENTS OF THE INVENTION

According to a first embodiment, the present invention relates to a mechanical transmission system, MTS (100), for a steerable tool (500) which steerable tool (500) has a proximal end (20) and distal end (40) and comprises a shaft region (532), a bendable proximal part, BPP (534) that is omnidirectionally moveable, and a bendable distal part, BDP, (530) that is omnidirectionally moveable and moves responsive to movement of the BPP (534), which MTS (100) comprises a plurality of longitudinal members, LM (110) each having a proximal (20) and distal end (40), arranged in a longitudinal direction around a fictive tube (120), and has a corresponding transmission shaft region, TSR (132), transmission bendable proximal part, TBPP (134) and transmission bendable distal part, TBDP (130), wherein a plane section (114) of at least one LM (110) demonstrates an anisotropic area moment of inertia, and the majority of the LMs (110) are each axially rotationally constrained at 1 or more constraining points along the TBDP (130) or along the TSR (132) wherein the LMs are longitudinally slidable with respect to each discrete constraining point, and the MTS (100) is configured such that the BDP (530) tip is axially rotationable in a bent position by a complementary rotation of the BPP (534).

At least one constraining point disposed along the TSR (132) may be provided in the distal half of the TSR (132), preferably in 10% of the TSR (132) total length located at the distal end of the TSR (132) and at least one other constraining point disposed along the TSR (132) may be provided in the proximal half of the TSR (132), preferably in 10% of the TSR (132) total length located at the proximal end of the TSR (132). Said the majority of the LMs (110) may be each further axially rotationally constrained at 1 or more constraining points along the TBPP (134). The MTS (100) may further be provided with one or more LM guides (300, 305, 350) each configured to axially rotationally constrain said majority of the LMs (110) at the constraining points. Each LM guide may be further configured to maintain said majority of the LMs (110) at an essentially constant circumferential position on the fictive tube (120) at the constraining points. The MTS (100) may be provided with at least 2 LM guides (300, 305, 350) in the TBDP (130) and at least 2 LM guides in the TBPP (134). The LM guide (300, 305, 350) may comprise a body provided with a plurality of discrete channels (310) arranged around the fictive tube (320, 120) configured to axially rotationally constrain said majority of the LMs (110) at the constraining point, and to maintain the LMs (110) at an essentially constant circumferential position on the fictive tube (120) at the constraining point. A channel (310) may be configured to axially rotationally constrain an LM (110) in the TBDP or TBPP contains a profile in transverse cross-section that complements the plane section (114) of the LM. The LM guides (300) in the TDBP (130) and TDPP (134) may be articulated LM guides (305, 305', 305") respectively tandemly arranged, and mutually articulated, thereby supporting bending of the LMs (110) in the DBP (130) and PBP (134) respectively. The articulated LM guides (305, 305', 305") may be in pairwise mutual contact through a pivot joint that comprises a ball and socket joint. Yawing between adjacent articulated LM guides may be limited to provide an essentially fixed mutual rotational alignment of the discrete constraining points along the fictive tube. The LM guides (300) in the TSR (132) may be fixed LM guides (350, 350', 350") and rotationally fixed with respect to each other to reduce the flexibility of TSR (132) compared with the flexibility of the TBDP (130) or TBPP (134). The plane section of the LM may be a rectangular, letter "I", or circular segment profile, optionally wherein one or more of the profile corners are pointed or rounded-off. The BDP (530) and BPP (534) may be at least partially curveable. According to a second embodiment, the present invention relates to a steerable tool (500) comprising an MTS (100) as defined herein.

Another embodiment of the invention relates to a mechanical transmission system, MTS (100), for a steerable tool (500) which steerable tool (500) has a proximal end (20) and distal end (40) and comprises a bendable distal part, BDP, (530) that moves omnidirectionally, responsive to actuation of the MTS (100) at the proximal end (20), which MTS (100) comprises a plurality of longitudinal members, LM (110) each having a proximal (20) and distal end (40), arranged in a longitudinal direction around a fictive tube (120), and has a corresponding transmission bendable distal part, TBDP (130), wherein a plane section of at least one, optionally each and every LM (110) demonstrates an anisotropic area moment of inertia, and the majority, preferably all, of the plurality of LMs (110) are each axially rotationally constrained in the transmission bendable distal part (130).

The anisotropy may be with respect to mutually perpendicular axes (116, 118) that intersect at a centroid of the plane section (114) of the LM (110), and wherein the axis (116) around which the LM (110) has the higher area moment of inertia is oriented in a direction towards a central axis (A-A') of the fictive tube (120). The axis (116) may intersect the central axis (A-A') of the fictive tube (120) or diverge from the central axis (A-A') of the fictive tube (120)

by adopting an angle (alpha) of up to 60 deg compared with an imaginary line draw (115) between the central (A-A') axis and the centroid (111) of the plane section. The plane section (114) may be present in the transmission bendable distal part (130). The number of LMs (110) may be at least three or four. The plane section (114) of the LM may have a rectangular, letter "I", or circular segment profile, optionally wherein one or more of the profile corners are pointed or rounded-off.

The MTS (100) may be further provided with one or more LM guides (300, 350) configured to maintain the LMs (110) at an essentially constant circumferential position on the fictive tube (120) and to axially rotationally constrain said majority of the LMs (110) in the TBDP (130). The LM guide (300, 305, 350) may comprise a body provided with a plurality of discrete channels (310) arranged around the fictive tube (320, 120) configured to maintain the LMs (110) at the essentially constant circumferential position on the fictive tube (120) and to axially rotationally constrain said majority of the LMs (110) in the TBDP (310). A channel (310) configured to axially rotationally constrain an LM (110) in the TBDP may contain a profile in transverse cross-section that complements the plane section (114) of the LM. Some of the LM guides (300) may be articulated LM guides (305, 305', 305") tandemly arranged in the TBDP (130), and mutually articulated, thereby supporting bending of the LMs (110) in the DBP (130). The articulated LM guides (305, 305', 305") may be in pairwise mutual contact through a pivot joint. Some of the LM guides (300) may be fixed LM guides (350, 350', 350") that are arranged in a transmission shaft region, TSR (132), adjacent to the TDBP (130), and are rotationally fixed with respect to each other. The MTS (100) may further comprise a transmission bendable proximal part, TBPP (134), for omnidirectional actuation by the user, that induces the omnidirectional movement response of the TBDP (130).

Another embodiment of the invention relates to a steerable tool (500) comprising an MTS (100) as defined herein. The BDP (530) may be configured for movement in at least two different intersecting planes responsive to actuation of the MTS (100) at the proximal end (20), wherein the steerable tool (500) is further provided with an end effector (540) at the distal end of the BDP (530), and the MTS (100) is configured such that the end effector (540) is rotationally fixed in relation to the BDP (530), and the end effector is rotatable when the BDP (530) is in a bent position by a complementary rotation of the proximal bending part (202). The end effector may be rotationally fixed in relation to the BDP by means of a lockable element configured to allow rotational adjustment of and to rotationally fix the end effector (540) in rotational relation to the BDP (530).

BRIEF DESCRIPTION OF THE FIGURES

FIG. 20 is an isometric view of a MTS 100 of the invention provided with 4 LMs maintained in radial position with a plurality of fixed and articulated LM guides.

FIG. 21A shows a bendable distal part of a mechanical transmission means, not of the invention disposed with circularly-profiled longitudinal members.

FIG. 21B shows the bendable distal part of a mechanical transmission means of FIG. 21A and not of the invention, in the undesirable and stable spiral kinematic chain state.

FIG. 22 shows two exemplary orientations of a LM guide channel and of the LM present therein.

FIGS. 22A and B show two exemplary orientations of a LM present in an LM guide channel.

FIG. 23 illustrates discrete constraining points in essentially fixed mutual rotational alignment along the fictive tube.

DETAILED DESCRIPTION OF INVENTION

Figure 1:
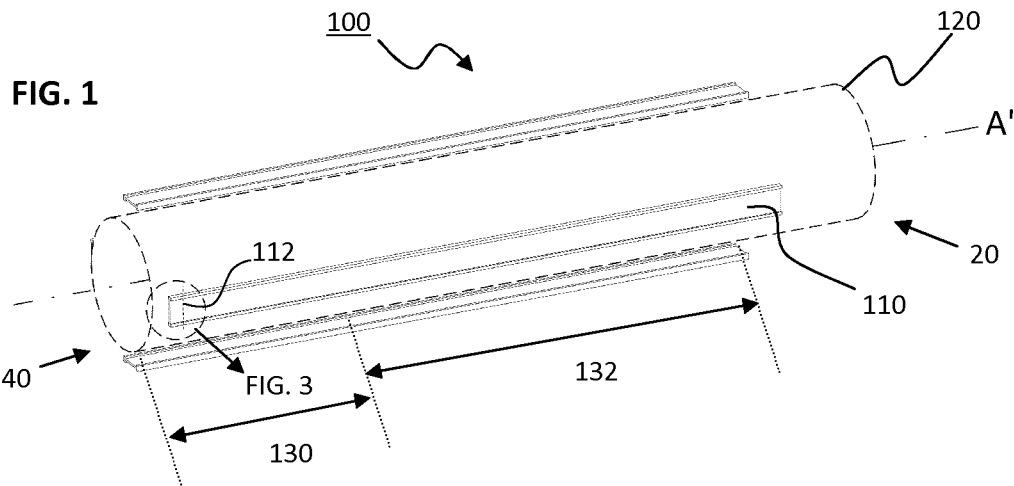
FIG. 1 depicts an isometric view of a mechanical transmission system (MTS) of the invention in isolation in a linear configuration.

Before the present method used in the invention is described, it is to be understood that this invention is not limited to particular methods, components, or devices described, as such methods, components, and devices may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. All publications referenced herein are incorporated by reference thereto. All United States patents and patent applications referenced herein are incorporated by reference herein in their entirety including the drawings.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

The terms "distal" and "proximal" are used through the specification, and are terms generally understood in the field to mean towards (proximal) or away (distal) from the surgeon's side of the apparatus. Thus, "proximal" means towards the surgeon's side and, therefore, away from the patient's side. Conversely, "distal" means towards the patient's side and, therefore, away from the surgeon's side.

The present invention relates to a mechanical transmission system (MTS) for a steerable tool. The steerable tool is preferably longitudinal, meaning it is longer in one direction. It does necessarily not imply the steerable tool is linear, though a linear (straight) steerable tool is within the scope of the invention. The steerable tool may be straight or curved, for instance, having a C- or S-shape shaft region.

Typically, a steerable tool has a proximal end and distal end and comprises a bendable distal part (BDP), sometimes known as a wrist, that moves responsive to actuation of the MTS at the proximal end. Actuation of the MTS at the proximal end induces a movement response in the BDP. The steerable tool is also provided with a shaft region (SR), that may be essentially rigid or semi-rigid, one end of which is disposed with the BDP. The shaft region is longitudinal, meaning it is longer in one direction. It does necessarily not imply the shaft region is linear, though a linear (straight) shaft is within the scope of the invention. The shaft region may be straight or curved, for instance, having a C- or S-shape. To control BDP, steering wires which are known as longitudinal members (LMs) are used in the MTS. They control the BDP by pulling or pushing. The MTS comprises a plurality of longitudinal members (LM) each having a proximal end and a distal end, arranged in a longitudinal direction around a fictive tube. At least one of the LMs contains a region, in which a plane section thereof has an anisotropic second moment of inertia with respect to two intersecting axes. The tip (distal terminal end) of the BDP should be able to move with equal ease in any direction i.e. there is no singularity. The movement response is proportion to the degree of actuation.

The shaft region (SR) is preferably essentially rigid or semi-rigid, or may be flexible and become rigid or semi-rigid when co-operating with a rigid or semi-rigid exotube or outer tube. The shaft region is adjacent to the BDP. The shaft region may contact the BDP. The steerable tool may further be provided with a bendable proximal part (BPP) at the proximal end of the steerable tool. The BPP is adjacent to the shaft region i.e. the shaft region is disposed between the BDP and BPP. The shaft region may contact the BPP. Movement of the BPP actuates the MTS at the proximal end and induces a movement response in the BDP. Movement of BPP in different radial directions and to different bending degrees is transmitted using the MTS to the BDP, and results in a corresponding change in radial direction and/or degree of bending of the BDP. The steerable tool may be actuated at the proximal end using an electromechanical device connected directly to the MTS, for instance to two or more of the LMs, or each and every LM. Typically the LMs in the shaft region would be actuated. In such case, the tool may be devoid of a BPP. Alternatively, robotic control may be realised by using an electromechanical device to actuate the BPP. The electromechanical device may be, for instance, a servo motor. Coupling to an electromechanical device would facilitate direct integration into a surgical robot.

The movement response of the BDP may be:
  a change in degree of bending within a plane parallel to and contacting a central longitudinal axis of and extending from the shaft region,
  a change direction of the bend within a plane perpendicular to and contacting a central longitudinal axis of and extending from the shaft region.

The combination of movements the steerable tool allows would normally facilitate a rotation of the shaft region that could be transmitted to BDP at its tip while the BDP is in a bent position. However, the inventors have found that the tip of BDP does not rotate synchronously with the shaft region. There is a "dead-zone", backlash or play where torque applied at the proximal end and transmitted through the shaft region does not result in a rotation of the BDP tip, particularly when it is in a bent position.

The steerable tool may be a surgical instrument, such as, for instance, a laparoscopic instrument or an endovascular catheter. The invention can be used in an articulated instrument such as but not limiting to endovascular applications, surgical instruments, robotic tele-operated medical robotics or hand-held surgical tools and industrial applications.

The BDP is configured to move omni-directionally i.e. in any radial direction. BDP is preferably configured to move in any radial direction (about 360° with respect to central longitudinal axis (A'-A) of the shaft region). The BDP is preferably configured to move in at least two different planes (e.g. 3, 4, 5, 6, 7, 8 or more) disposed parallel to and contacting a central longitudinal axis (A'-A) of the shaft region. Preferably, the BDP is configured to move in an infinite number of different planes disposed parallel to and contacting a central longitudinal axis (A'-A) of the shaft region. The BDP bending is typically at least partially a curve i.e. the BDP is curvable. By curve, it is meant there is a smooth bending rather than angular bending as is commonly understood in the art. A curve typically contains for at least a portion of its length a continuously changing (e.g. increasing or decreasing) gradient, compared with an angular bend that typically exhibits a constant gradient or a discrete and singular change of gradient, for instance, at a hinge joint. It is appreciated that the BDP may biased in a straight configuration and actuation induces curvature therein. Alternatively, the BDP may biased in a curve and actuation induces additional or less curvature therein.

Similarly, the BPP, where present, is configured to move omni-directionally i.e. in any radial direction. BPP is preferably configured to move in any radial direction (about 360° with respect to central longitudinal axis (A'-A) of the shaft region). MTS is preferably configured to move the BPP in at least 8 different directions. The BPP is preferably configured to move in at least two different planes (e.g. 3, 4, 5, 6, 7, 8 or more) disposed parallel to and contacting a central longitudinal axis (A'-A) of the shaft region. Preferably, the BPP is configured to move in an infinite number of different planes disposed parallel to and contacting a central longitudinal axis of the shaft region. The BPP bending is typically at least partially a curve i.e. the BPP is curvable. By curve, it is meant there is a smooth bending rather than angular bending as is commonly understood in the art. A curve typically contains for at least a portion of its length a continuously changing (e.g. increasing or decreasing) gradient, compared with an angular bend that typically exhibits a constant gradient or a discrete and singular change of gradient, for instance, at a hinge joint. It is appreciated that the BPP may biased in a straight configuration and actuation induces curvature therein. Alternatively, the BPP may biased in a curve and actuation induces additional or less curvature therein.

The steerable tool may be provided with an end effector such as grip, pliers, cutting scissors and the like. The end effector is provided at the distal end of the steerable tool.

Furthermore it may be possible to rotate the distal tip of the instrument about its own axis i.e. axially even in a bent status. Accordingly, the MTS may be configured such that BDP (or TBDP) tip is axially rotationable in a bent position by a complementary rotation of the BPP (or TBPP). The steerable tool may be provided with an end effector at the distal end of the BDP wherein the MTS is configured such that the end effector is rotationally fixed in relation to the BDP, and the end effector is rotatable when the BDP is in a bent position, by a complementary rotation of the BPP. The end effector may be rotationally fixed in relation to the BDP by means of a lockable element configured to allow rotational adjustment of and to rotationally fix the end effector in rotational relation to the BDP.

The MTS as described herein has a proximal end and distal end. The distal end is provided with a transmission bendable distal part (TBDP) that that moves responsive to actuation of the MTS at the proximal end, and which moves the BDP of the steerable tool. The TBDP corresponds in position with the BDP. The proximal end may be provided with a transmission bendable proximal part (TBPP). Movements by the user of the BPP of the steerable tool are transferred to the TBPP. The TBDP corresponds in position with the BPP. The TBPP actuates the MTS at the proximal end and induces the movement response of the TBDP that is transferred to the BDP of the steerable tool.

The MTS is also provided with a transmission shaft region (TSR) to be disposed within the corresponding shaft region of the steerable tool. The TSR is preferably essentially rigid or semi-rigid, or may become rigid or semi-rigid when co-operating with a rigid or semi-rigid exotube or outer tube.

The MTS may be actuated at the proximal end using an electromechanical device connected directly to the MTS, for instance to two or more of the LMs, or each and every LM. Typically the LMs in the LM shaft region would be actuated. In such case, the tool may be devoid of a TBPP. Alternatively, robotic control may be realised by using an electromechanical device to actuate the BPP. The electromechanical device may be, for instance, a servo motor. This would facilitate direct integration into a surgical robot.

The MTS is preferably configured to move the BDP omni-directionally. MTS is preferably configured to move the BDP in any direction (about 360° with respect to central longitudinal axis (A'-A) of the TSR). MTS is preferably configured to move the BDP in at least 8 different directions. The MTS may be configured to move the BDP in at least two different planes (e.g. 3, 4, 5, 6, 7, 8 or more) disposed parallel to and contacting a central longitudinal axis (A'-A) of the TSR. Preferably, MTS is configured to move the BDP in an infinite number of different planes disposed parallel to and contacting a central longitudinal axis (A'-A) of the transmission shaft region.

The TBDP is configured to move omni-directionally i.e. in any radial direction. TBDP is preferably configured to move in any radial direction (about 360° with respect to central longitudinal axis (A'-A) of the shaft region). The TBDP is preferably configured to move in at least two different planes (e.g. 3, 4, 5, 6, 7, 8 or more) disposed parallel to and contacting a central longitudinal axis (A'-A) of the shaft region. Preferably, the TBDP is configured to move in an infinite number of different planes disposed parallel to and contacting a central longitudinal axis (A'-A) of the shaft region. The TBDP bending is typically at least partially a curve i.e. the TBDP is curvable. By curve, it is meant there is a smooth bending rather than angular bending as is commonly understood in the art. A curve typically contains for at least a portion of its length a continuously changing (e.g. increasing or decreasing) gradient, compared with an angular bend that typically exhibits a constant gradient or a discrete and singular change of gradient, for instance, at a hinge joint. It is appreciated that the TBDP may biased in a straight configuration and actuation induces curvature therein. Alternatively, the TBDP may biased in a curve and actuation induces additional or less curvature therein.

The TBPP is configured to move omni-directionally i.e. in any radial direction. TBPP is preferably configured to move in any radial direction (about 360° with respect to central longitudinal axis (A'-A) of the shaft region). The TBPP is preferably configured to move in at least two different planes (e.g. 3, 4, 5, 6, 7, 8 or more) disposed parallel to and contacting a central longitudinal axis (A'-A) of the shaft region. Preferably, the TBPP is configured to move in an infinite number of different planes disposed parallel to and contacting a central longitudinal axis (A'-A) of the shaft region. The TBPP bending is typically at least partially a curve i.e. the TBPP is curvable. By curve, it is meant there is a smooth bending rather than angular bending as is commonly understood in the art A curve typically contains for at least a portion of its length a continuously changing (e.g. increasing or decreasing) gradient, compared with an angular bend that typically exhibits a constant gradient or a discrete and singular change of gradient, for instance, at a hinge joint. It is appreciated that the TBPP may biased in a straight configuration and actuation induces curvature therein. Alternatively, the TBPP may biased in a curve and actuation induces additional or less curvature therein.

Furthermore it may be possible to rotate the distal tip of the instrument about its own axis even in a bent status. The MTS may be provided with an end effector at the distal end of the TBDP wherein the MTS is configured such that the end effector is rotationally fixed in relation to the TBDP, and the end effector is rotatable when the TBDP is in a bent position, by a complementary rotation of the TBPP. The end effector may be rotationally fixed in relation to the TBDP by means of a lockable element configured to allow rotational adjustment of and to rotationally fix the end effector in rotational relation to the TBDP.

The MTS comprises a plurality of longitudinal members (LMs) each having a proximal end and a distal end, arranged in a longitudinal direction around a fictive tube. The fictive tube is a geometric shape around which the LMs are aligned. It is preferably longitudinal. It preferably has a circular transverse-cross section, a transverse cross-section being essentially perpendicular to a longitudinal axis. A central axis (A'-A) of the fictive tube is preferably coaxial with a central axis of the steerable tool. The fictive tube is preferably cylindrical. The fictive tube has diameter that is smaller than the diameter of the steerable tool at the corresponding position.

The LM as described herein has a proximal end and distal end. The distal end is provided with a LM bendable distal part (LMBDP) to be disposed in the TBDP of the MTS. The LM is provided with a LM shaft region (LMSR) to be disposed in the corresponding TSR of the MTS. The LMSR is proximal to and adjacent to the LMBDP. The proximal end may be provided with a LM bendable proximal part (LMBPP) to be disposed in the TBPP of the MTS.

The distal ends of the LMs are maintained in fixed relation to each other in the MTS. The distal ends of the LMs, more preferably the distal terminal ends of the LMs, may be connected to a distal LM fixation element. Preferably, the distal LM fixation element maintains the LMs at their respective circumferential positions, for instance, it may maintain the distal terminal ends of the LMs in an annular ring. The distal LM fixation element may be, for instance, a disc or annulus disposed at the distal end of the MTS.

Similarly, the proximal ends of the LMs, more preferably the proximal terminal ends of the LMs, may be maintained in fixed relation to each other in the MTS. The proximal ends of the LMs may be connected to a proximal LM fixation element. Preferably, the proximal LM fixation element maintains the LMs at their respective circumferential positions, for instance, it may maintain the proximal terminal ends of the LMs in an annular ring. The proximal LM fixation element may be a disc or annulus disposed at the proximal end of the MTS.

The LMs are slidable relative to each other, to the extent that movement is restricted by said LM fixation element(s). The application of force—pushing and/or pulling—at the proximal end of the MTS is transmitted via the LMs along the LMSR to the LMBDP which in turn causes movement of the TBPP e.g. by pulling or pushing the aforementioned fixation element(s). The number of LMs in an MTS may be at least two, for instance, 2, 3, 4, 5, 6, 7, 8, 9, 10, 11, 12, 13, 13, 14, 15, 16, 17, 18, 19, or 20, or more. For omni-directional steering, it is preferred that at least 4, more preferably at least 6 or 8 LMs are present.

Dimensions of an LM can may depend on the diameter and length of the eventual steerable tool, and on the number of LMs utilised. As a general guidance, an LM may have a thickness in one direction of 40 µm, 50 µm, 60 µm, 80 µm, 100 µm, 200 µm, 200 µm, 400 µm or 500 µm, or a value in the range between any two of the aforementioned values. An LM may have a width of 80 µm, 100 µm, 120 µm, 140 µm, 160 µm, 180 µm, 200 µm, 300 µm, 400 µm, 500 µm, 600 µm, 700 µm, 800 µm, 900 µm, 1000 µm, 1100 µm, 1200 µm, 1300 µm, 1400 µm, or 1500 µm or a value in the range between any two of the aforementioned values. The skilled person would understand how to select a suitable thickness and width according to the diameter of the MTS. For a 10 mm diameter MTS, the preferred thickness is 280 µm to 320 µm, preferably about 300 µm, and the preferred width is 480 µm to 520 µm, preferably about width 500 µm in the LMBDP, LMSR and optionally LMBPP. The length of the MTS will depend on the length of the steerable tool and its application. The above preferred dimensions apply to MTS of 37-40 cm in length.

The LMs may be made from any suitable material having the appropriate tensile and compression properties and can be deduced by the person skilled in the art. Examples include stainless steel or nitinol, beta titanium, spring steel, or polymer.

The LM may be made from a single strand of a material e.g. a single strip of stainless steel. Alternatively, it may be made from multiple strands of material tandemly connected.

The LMs are longitudinally arranged around the fictive tube. The LMs may be distributed evenly around the fictive tube e.g. the distance between adjacent LMs may be essentially the same. The LMs may distributed symmetrically around the fictive tube e.g. there may be a plane of symmetry about a longitudinal-cross section of the fictive tube. The LMs may be distributed unevenly around the fictive tube e.g. the distance between at least two pairs of adjacent LMs may be different.

The LM is preferably disposed essentially along the length of the MTS, and of the steerable tool. It spans the TBDP and extends into the TSR, and the TBPP where present.

The LMs are preferably arranged such that their longitudinal axes are mutually parallel. The LMs are preferably arranged such that their longitudinal axes are parallel to a longitudinal axis (A-A') of the fictive tube. The LMs are preferably arranged such that their longitudinal axes are parallel to a longitudinal axis of the longitudinal steerable tool.

At least one plane section of the LM demonstrates an anisotropic area moment of inertia. A plane section is typically a transverse cross-section perpendicular to the longitudinal central (z) axis of an LM (see FIG. 3). The anisotropy is with respect to mutually perpendicular axes (x, y) that intersect at a centroid of the plane section, and which axis form a plane that is parallel to and lies on the plane section. The centroid is understood to be the geometric centre of the plane section, more specifically of the outer profile of the plane section. When the plane section has an essentially rectangular profile, the x and y axes are aligned parallel to the straight edges of the rectangle, the x-axis being aligned such that the area moment of inertia in respect of the x-axis is the greatest. When the plane section has an irregular profile, the x-axis is aligned such that the area moment of inertia is greatest with respect to the x-axis. Preferably the ratio of the area moment of inertia ($I_r$) with respect to an x-axis ($I_x$) and a y-axis ($I_y$) ($I_x/I_y$) which intersect a centroid of a plane section of the LM is greater than 1, or is about 1.1, 1.5, 2, 2.5, 3, 3.5, 4, 4.5, 5, 5.5, 6, 6.5, 7, 8, 9, 10, 11, 12, 13, 14, 15, 16, 17, 18, 19, or 20 or more, or a value in the range between any two of the aforementioned values. As a general guidance, Ir may be between 1.1 and 4, preferably between 2 and 3 for an invasive surgical instrument which the inventors have found provides a stable TDBP that is resistant to torque, while being amenable to bending, and stills avoids the undesirable spiral kinematic chain state.

The at least one plane section may be in the LMBDP. Preferably, the LMBDP demonstrates the anisotropic property at multiple plane sections, preferably at the majority of, or substantially all positions along the length of the LMBDP. Preferably, the LMBPP demonstrates the anisotropic property at multiple plane sections, preferably at the majority of, or substantially all positions along the length of the LMBPP. Preferably, the LMSR demonstrates the anisotropic property at multiple plane sections, preferably at the majority of, or substantially all positions along the length of the LMSR. According to one aspect, the LMBDP, and 1 to 10% of the length of the TSR from its distal end demonstrate the anisotropic property at the majority of, or substantially all plane sections therein. Where in the LMBPP is also present, the LMBDP, and 1 to 10% of the length of the TSR from its distal end, the LMBPP, and 1 to 10% of the length of the TSR from its proximal end, demonstrate the anisotropic property at the majority of, or substantially all plane sections therein.

The LM is preferably orientated in the MTS or steerable tool such that the axis (typically the x-axis) having the higher area moment of inertia extends towards the central (A-A') axis of the fictive tube of the MTS, or of the steerable tool. While such axis extends towards the central (A-A') axis, it may or may not intersect the central A-A' axis. It may diverge from the central axis, for instance, the x-axis may adopt an angle (alpha) of 10 deg, 20 deg or 30 deg, up to 60 deg compared with an imaginary line draw between the central (A-A') axis of the fictive tube of the MTS and the centroid of the plane section (see FIG. 22). In other words the LM is preferably orientated such that the axis (typically the y-axis) having the lower area moment of inertia essentially faces the central (A-A') axis of the fictive circle of the MTS, or of the steerable tool.

Exemplary profiles (outer shape) of the planar transverse cross-section that demonstrate the aforementioned anisotropic area moment of inertia include rectangular, letter "I", circular segment (e.g. semicircle, quarter circle etc). One or more, preferably all of the corners of the profiles may be pointed (e.g. square) or rounded-off. In the case of a rectangular LM, the radius of an edge may be up to 10%, 20%, 30%, 40% or 50% of length of the shorter side of rectangle. Typically, it will be 10 µm, 20 µm, or 30 µm or more, for instance, between 10 µm and 200 µm.

The area moment of inertia is also known as the second moment of inertia, moment of inertia of plane area, polar moment of area or second area moment. For a LM of uniform material, the anisotropic property is determined essentially by the outer shape of the plane section. It can be calculated from the geometry of the plane section using techniques well known in the art. For instance, $I_x$ and $I_y$ can be calculated using Eqs 1 and Eqs 2, where x, and y are the coordinates of the differential element of dA, and A is the area of the plane section, x and y-axes intersect at a centroid of the plane section.

$$I_x = \int y^2 dA \qquad [Eq\ 1]$$

$$I_y = \int x^2 dA \qquad [Eq\ 2]$$

An LM having an isotropic area moment of inertia would facilitate omnidirectional movement at the TBDP and TBPP, since the LM needs to be able to bend in all directions, not only in respect of circumferentially opposing actuating LMs (anterior and posterior LMs) that apply a pulling or pushing force that bends at the TBDP, but in respect of those LMs arranged between the actuating LMs—i.e. the lateral LMs. An LM having an isotropic area moment of inertia would reduce resistance to bending of these lateral LMs, and hence is preferred in the art. Contrary to this, the inventors have found that the MTS tolerates LMs having an anisotropic area moment of inertia, and which require more force to bend lateral LMs in the TBDP and TBPP because they bend over a larger radius compared with the LMs located on the inside of the bend (see FIG. 16).

Additionally, the inventors have found that axial rotation of the TSR is transmitted synchronously to the TBDP when LMs having an anisotropic area moment of inertia are employed. This is less the case when LMs having an isotropic area moment of inertia are used, which can result in a rotational lag—also known as backlash or play—before movements are transmitted to the tip of the TBDP. For instance, where a mechanical transmission means contains longitudinal members that have a circular transverse profile, an axial rotation of the end effector in respect of the shaft results in a torsion of the individual longitudinal members, that in turn means a torque applied to the steerable tool at one end is not transmitted to the other end, since said torque is absorbed by said circular-profiled longitudinal members (see, for instance FIG. 13). A counter torque force is induced that is inverse-linearly proportional to the length of torsion. In case of a steerable tool with a distal bendable part of 20 mm and a shaft region of 400 mm, a 45° torsion of the circular-profile longitudinal members will be spread over a distance of 420 mm, allowing significant backlash or play. The surgeon must apply additional torque before the slack is taken up.

For the same mechanical transmission system, but where anisotropic LMs are used, there is reduced torsion in the individual LMs, since the anisotropy provides each LM with an enhanced resistance against twisting. This effect is enhanced when combined with LM guides, mentioned below, that constrain each LM to prevent or reduce axial rotation. Hence, the amount of backlash is reduced.

In a preferred aspect, the majority, preferably all of the LMs in the plurality of LMs are each axially rotationally constrained at 1 or more constraining points (or regions) along the longitudinal axis of the fictive tube of the MTS.

Preferably, there is at least one 1 constraining point present along the TBDP or along the TSR. The at least one constraining point disposed along the TSR may be provided in the distal half of the TSR, preferably in 25% or 10% of the TSR total length located at the distal end of the TSR, optionally at the distal tip of the TSR. Constraining point or points disposed along the TSR may be confined to the distal half of the TSR, preferably in 25% or 10% of the TSR total length located at the distal end of the TSR, optionally at the distal tip of the TSR. Preferably, there are at least 2 constraining points, at least 1 disposed along the TSR, and at least 1, 2, 3 or 4 disposed along the TBDP.

Preferably, there is at least one 1 constraining point present along the TBPP or along the TSR. The at least 1 constraining point disposed along the TSR may be provided in the proximal half of the TSR, preferably in 25% or 10% of the TSR total length located at the proximal end of the TSR, optionally at the proximal tip of the TSR. Constraining point or points disposed along the TSR may be confined to the proximal half of the TSR, preferably in 25% or 10% of the TSR total length located at the proximal end of the TSR, optionally at the proximal tip of the TSR. Preferably, there are at least 2 constraining points, at least 1 disposed along the TSR and at least 1, 2, 3 or 4 disposed along the TBPP.

There may be at least 4 constraining points, at least 1 disposed along the TBDP, at least 1 disposed along the TSR in the distal half of the TSR, preferably in 25% or 10% of the TSR total length located at the distal end of the TSR, optionally at the distal tip of the TSR, at least 1 disposed along the TBPP, and at least 1 disposed along the TSR in the proximal half of the TSR, preferably in 25% or 10% of the TSR total length located at the proximal end of the TSR, optionally at the proximal tip of the TSR, In the TBDP or BDP (or TBPP or BPP), the constraining points are discrete. By discrete it is meant they are spatially separated in the direction of the central longitudinal (A-A') axis of the fictive tube. The discrete constraining points are spatially separated in the direction of the central longitudinal (A-A') axis of the fictive tube in the TBDP or BDP or TBPP (or BPP where present).

In the TSR or SR constraining points may or may not be discrete. When not discrete they may be provided, for instance, as a continuous longitudinal channel in the direction of the central longitudinal (A-A') axis of the fictive tube in the TSR or SR.

Figure 12:
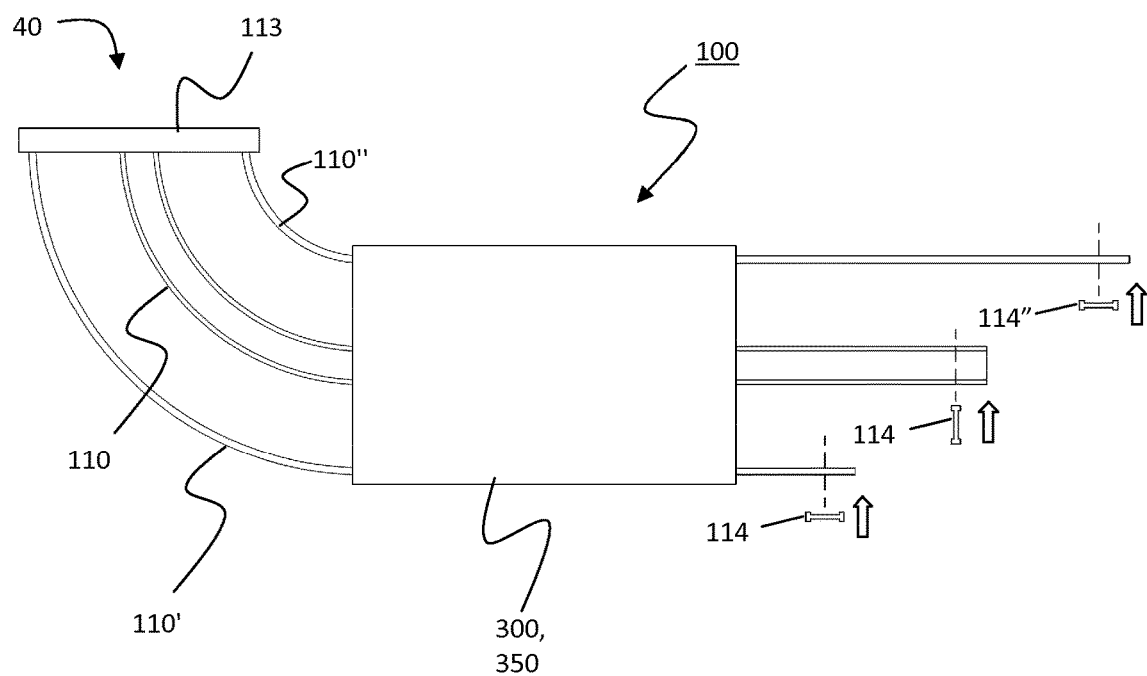
FIG. 12 depicts a side view of a MTS of the invention, in which the LMs each have "I"-shaped plane sections.

It is appreciated that the aforementioned constraining is different from any constraining effect provided by the LM fixation element; the LM fixation element fixes the position of LM and does not allow the LMs to slide relative to each other (e.g. FIG. 12, distal LM fixation element 113).

For the plurality of LMs, it allows the LM to be slidable with respect each other at each of said constraining points. As described later below, a constraining point may be provided by an LM guide, in particular an articulated LM guide in TBDP or BDP (and in the TBDP or BDP where present) or a fixed LM guide in the SR or TSR.

It is a further aspect that the constraining points may be in essentially fixed mutual rotational alignment; they are in essentially mutually fixed axial rotational alignment along the fictive tube. By essentially mutual fixed rotational alignment or essentially fixed mutual axial rotational alignment, it is meant that the axial (A-A') rotation angle between adjacent (neighbouring) constraining points along the fictive tube is essentially fixed or limited. For a plurality of constraining points arranged longitudinally along the fictive tube, the radial angle of the LM with respect the central longitudinal axis (A-A') of the fictive tube remains the same at each constraining point in an actuated or unactuated state. The constraining points may be in essentially fixed alignment when no working load is applied to the MTS or to the steerable tool.

According to one aspect of the invention, the constraining points are in essentially fixed mutual rotational alignment such that a radial line intersecting a discrete constraining point at the distal terminal end of a TBDP shows a deviation angle, epsilon, of no more than 30 deg, preferably 25 deg along the longitudinal axis of the fictive tube compared with that of a constraining point at the proximal terminal end of a TBDP or in the TSR at the distal end (see FIG. 23 e.g. I-A cf I-E). The radial line radiates from and is perpendicular to the central longitudinal axis (A-A') of the fictive tube. For the constraining points in question (e.g. a channel) the point of intersection is the same to enable a comparison.

According to one aspect of the invention, the constraining points are in essentially fixed mutual rotational alignment such that a radial line intersecting a discrete constraining point at the proximal terminal end of a TBPP shows a deviation angle, epsilon, of no more than 30 deg, preferably 25 deg along the longitudinal axis of the fictive tube compared with that of a constraining point at the distal terminal end of a TBPP or in the TSR at the proximal end. The radial line radiates from and is perpendicular to the central longitudinal axis (A-A') of the fictive tube. For the constraining points in question (e.g. a channel) the point of intersection is the same to enable a comparison.

According to another aspect, a radial line intersecting a discrete constraining point shows a deviation angle, epsilon, of no more than 10 deg, preferably 5 deg compared with that of an adjacent (nearest neighbour) discrete constraining point along the longitudinal axis of the fictive tube (e.g. FIG. 23. I-C cf I-D). The radial line radiates from and is perpendicular to the central longitudinal axis (A-A') of the fictive tube. Between adjacent discrete constraining points (e.g. a channel) the point of intersection is the same to enable a comparison. Besides the discrete constraining points in the TBDP or BDP (and in the TBPP or BPP where present) being mutually essentially axially rotational fixed along the fictive tube, they may be essentially axially rotational fixed with respect to constraining points in the SR or TSR.

An essentially fixed mutual rotational alignment in the TBDP or BDP (and in the TBPP or BPP where present) may be provided, for instance, by the presence of the LM's which limit the amount of rotation between adjacent LM guides.

An essentially fixed mutual rotational alignment in the TBDP or BDP (and in the TBPP or BPP where present) may be provided, for instance, by articulated LM guides wherein yawing between adjacent articulated LM guides is limited or prevented as described later below.

An essentially fixed mutual rotational alignment in the SR or TSR is provided, for instance, by fixed LM guides wherein yawing between adjacent fixed LM guides is limited or prevented as described later below.

The discrete constraining points TBDP or BDP (and in the TBPP or BPP where present) being in essentially fixed mutual rotational alignment may further contribute to the reduction in backlash.

The obtained joint stiffness in the DBP is largely dependent on the anisotropic area moment of inertia (Iy) of the LMs. Other factors can influence the stiffness, including the elastic modulus, shear modulus, the number of Lms, the distance of the LM to the central axis of the MTS, length of the LM section, the polar moment of inertia.

The counter-acting force is proportional to the area moment of inertia (I). The inertia is related to the length of the long side of the planar section of the LM to the third power. This explains why the use of, for instance, an "I"-shape profile LM with a long and short side is advantageous. The long side of the plane section gives rise to a higher area moment of inertia in comparison to a standard round steering wire for the same cross section area. We call this the 'ruler' effect. Such a ruler can be easily bent in one direction. However in the other direction it is highly stiff. It is the latter stiffness that is used to block axial rotation deformations, and reduce backlash in the system.

Figure 3:
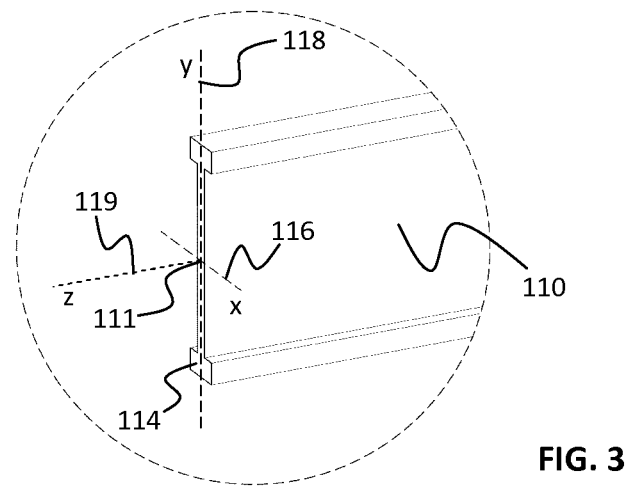
FIG. 3 depicts two intersecting axes on a plane section that is a planar transverse cross-section of the longitudinal member (LM) at position 112 in FIG. 1, which cross-section has an "I"-shaped profile.

Due to the profile of an LM, it cannot freely rotate at the constraining points; once the LM contacts a wall of a channel (e.g. FIG. 22B), rotation is prevented and a second effect comes into action, namely twisting of the strip around the z-axis (see FIG. 3). The torsional constant (measure of resistance against torsion) is called the polar moment of inertia, and equals to the sum of Ix and Iy (second moments of inertia, measure of resistance against bending). There is a third effect arising when an LM in only x-direction hits the wall of the LM guide (FIG. 22A, with LM for instance moved to the left so it touches the wall of the LM guide). This condition is met very quickly as the LM guide is positioned near the outer surface of the instrument, at a radial distance which is much larger than the thickness of the LM. The LM guide bends over its most bent resistive side (anisotropic moment of inertia) (see FIG. 14, 110). The torsional constant for this effect depends on: Iy, radius of instrument (distance of the center of the LM to the central axis of the instrument) squared and inversely to the length of the LM (distance between 2 constraining points) squared. Because the distance between the constraining points is of the same order compared to the radius of the instrument, and because the Iy is high due to the anisotropy and because the radius is large compared to the dimensions of the cross section of the LM, this third effect is very important. It tends to be much larger than the second effect, which explains the advantage of the anisotropic feature of the LM.

A rectangular-profiled LM with a thickness of 300 µm and a width of 530 µm, for instance, has the same cross-sectional area as a round wire of diameter 437 µm. However the area moment of inertia over the elongated side (oriented parallel to the circumference of the instrument) of the rectangular strip is twice the area moment of inertia of the round wire resulting in a double increase in rotational stiffness TBPP or the BPP ($300\times530=pi\times218^2$) ($1530=300\times530^3/12$) ($1437=437$ 4th$\times$pi/64).

Not only does the anisotropic area moment of inertia reduce axial rotation and hence backlash, it also reduces the formation of a spiral kinematic chain within the LMBDP (and hence the TBDP and BDP) or within the LMBPP (and hence the TBPP and BPP). The spiral kinematic chain is an undesirable configuration in the LMBDP or the LMBPP in which articulated LM-guides, despite being mutually rotationally constrained, adopt a mechanically stable configuration in which the promixal-most LM-guide is revolutely offset compared with the distal-most LM-guide (see FIGS. 21A and 21B). Such stable configuration is realised when the LM-guides constitute a kinematic chain that follows a spiral path. Omni-directional instruments based on a concatenation of articulated LM-guide are all prone to this phenomenon. In the case of surgical instruments this results in a rotation between shaft and end bendable distal part. In surgery this loss of revolute transmission is highly undesirable. The present inventors have found that LMs having an anisotropic area moment of inertia avoid the formation of this stable configuration. The effect is enhanced when the constraining points in the SR (TSR) and TBDP (BDP) and in the TBDP or BDP where present) are in essentially fixed mutual rotational alignment.

The LMs at the inside and the outside of a turn of a bent TBPP or BPP and which are the principal LMs involved in the transmission of force, bend over the axis with the smallest area moment of inertia. The side-disposed or lateral LMs, not involved not directly involved in the transmission of force, have to bend over the stiffer axis (see FIG. 12). In the case of a 10 mm diameter TBPP or BPP bent at 90° deflection the inner bending radius can be 5 mm while the bending radius in the middle will be 10 mm. Hence, the unfavorable bending over the elongated side of the anisotropic LM can be compensated by an increased bending radius.

The MTS may be provided with a plurality (e.g. 2 to 30, 3 to 20) of LM guides configured to support and maintain the arrangement of LMs around the fictive tube. In particular, the plurality of LM guides maintain the majority of, preferably all of the LMs at a constant circumferential position on the fictive tube. By maintaining a constant circumferential position, it is meant that a radial angle adopted by an LM with respect to a central longitudinal axis (A-A') of the fictive tube is essentially constant and that the radial distance of an LM from the central longitudinal axis (A-A') of the fictive tube is essentially constant. The LM guide is configured to maintain the essentially constant circumferential position in an actuated or unactuated state.

In particular, the plurality of LM guides may axially rotationally constrain the majority of, preferably all of the LMs, in particular at the TBDP (and TBPP where present), but also at the TSR. By axially rotationally constraining an LM it is meant that rotation of an LM around its longitudinal (axial) axis is constrained, for instance, at a constraining point. The LM guide is configured to maintain the essentially constant axial rotational angle in an actuated or unactuated state. An axial rotational angle, beta, (see FIGS. 22A and 22B) refers to an angle adopted by a plane section of the LM, for instance within the constraining point. A plane section is typically a transverse cross-section perpendicular to the longitudinal central (z) axis of an LM (see FIGS. 22A and B). The axial rotational angle, beta, is with respect to an x-axis of mutually perpendicular axes (x, y) that intersect at a centroid of the plane section, and which axis form a plane that is parallel to and lies on the plane section. The centroid is understood to be the geometric centre of the plane section, more specifically of the outer profile of the plane section. When the plane section has an essentially rectangular profile, the x and y axes are aligned parallel to the straight edges of the rectangle, the x-axis being aligned such that the area moment of inertia in respect of the x-axis is the greatest. When the plane section has an irregular profile, the x-axis is aligned such that the area moment of inertia is greatest with respect to the x-axis. Beta is a change in angle of x-axis (e.g. x' compared with x in FIG. 22B). For an essentially constant axial rotational angle i.e. where the LM is axially rotationally constrained, beta, typically has a deviation of between ±45 deg.

An LM guide in the BDP/TBDP (and BPP/TBPP where present) contains the aforementioned discrete constraining point for an LM to axially rotationally constrain an LM and to further maintain the LM at an essentially constant circumferential position on the fictive tube, wherein LMs are longitudinally slidable with respect to each discrete constraining point. For the plurality of LM, it allows the LM to be slidable with respect each other at each of said discrete constraining points.

Similarly, an LM guide in the shaft region or TSR contains the aforementioned discrete constraining point for an LM to axially rotationally constrain an LM and to further maintain the LM at an essentially constant circumferential position on the fictive tube, wherein LMs are longitudinally slidable with respect to each discrete constraining point. For the plurality of LM, it allows the LM to be slidable with respect each other at each of said discrete constraining points.

Some LM guides ("articulated LM guides" herein) may be articulated with respect to each other, particularly mutually pivoted, thereby supporting bending of the LMs, akin to a wrist joint. Articulated LM guides may be disposed in the TBDP and in the TBPP where present, corresponding to the BDP and the BPP of the steerable tool. An articulated LM guide may be articulated at one or both sides.

One or more LM guide ("fixed LM guides" herein) may be rotationally fixed with respect to each other, thereby maintaining a fixed (non-bending) path of the LM. They may rotationally fixed with respect to each other to reduce the flexibility of TSR compared with the flexibility of the TBDP. The rotation fixation prevent mutual rotation in any of the three axes (e.g. rolling, pitching and yawing). Fixed LM guides may be disposed in the TSR, corresponding to the SR of the steerable tool, giving rise to an essentially rigid or semi-rigid TSR.

As mentioned above, the TSR may become rigid or semi-rigid when co-operating with a rigid or semi-rigid exotube or outer tube. In other words, the TSR may be flexible. Rigidly may be applied by inserting the TSR into a rigid or semi-rigid tube, or by clamping a rigid or semi-rigid tube around the TSR. Hence, articulated LM guides may be disposed in the TSR, corresponding to the SR of the steerable tool.

An LM guide comprises a body having a distal side and a proximal side, and an outer edge or surface connecting the distal and proximal sides.

Figure 18:
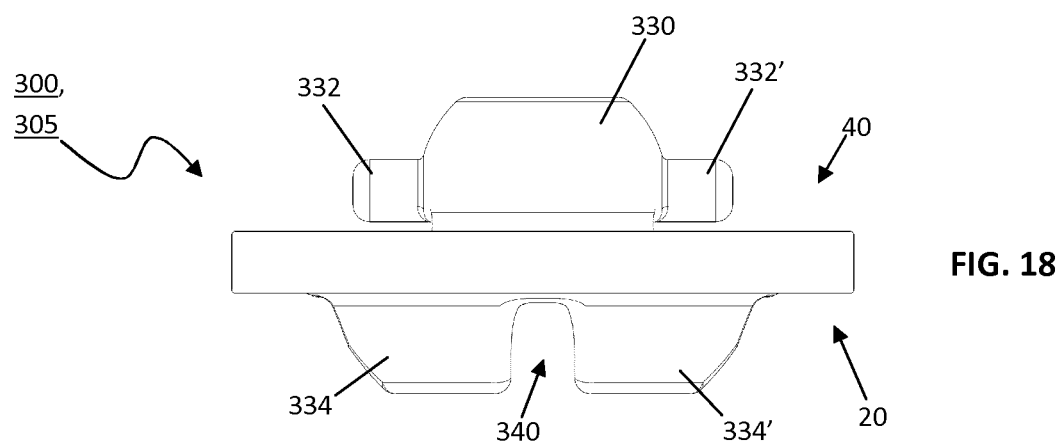
FIG. 18 is a side view of a LM guide that is an articulated LM guide.

For an articulated LM guide, the body is preferable substantially disc-shaped as shown, for instance, in FIG. 18. The disc may be disposed at a distal side with a socket and at a proximal side with a protrusion (e.g. ball) for engagement with a socket of an adjacent LM guide. Adjacent articulated LM guides hence form a ball and socket joint for mutual pivoting. As a general guidance for instruments such as surgical instruments, a disc may have a diameter of 0.1 cm, 0.2 cm, 0.3 cm, 0.4 cm, 0.5 cm, 0.6 cm, 0.8 cm, 1 cm, 1.2 cm, 1.4 cm, 1.6 cm, 1.8 cm, 2 cm or more, or a value between any two of the aforementioned values, preferably between 0.2 cm and 1.6 cm. The disc, excluding protrusions may have a thickness of 0.02 cm, 0.15 cm, 0.2 cm, 0.4 cm, or a value between any two of the aforementioned values, preferably between 0.1 mm and 0.2 mm.

For a fixed LM guide, the body is preferable substantially cylindrically shaped, the ends of the cylinder being the distal and proximal sides. As a general guidance for instruments such as surgical instruments, a cylinder may have a diameter of 0.1 cm, 0.2 cm, 0.3 cm, 0.4 cm, 0.5 cm, 0.6 cm, 0.8 cm, 1 cm, 1.2 cm, 1.4 cm, 1.6 cm, 1.8 cm, 2 cm or more, or a value between any two of the aforementioned values, preferably between 0.2 cm and 1.6 cm. The diameter of the articulated LM guide and the fixed LM guide may be the same.

The length of the cylinder may be, for instance, 0.5 cm, 0.6 cm, 0.8 cm, 1 cm, 2 cm, 3 cm or more, or a value between any two of the aforementioned values, preferably between 1 cm and 3 cm. While it is preferred that a plurality of tandemly arranged, fixed LM guides is present, it is within the scope of the invention that a single, long fixed LM guide is disposed in the TSR, corresponding to the SR of the steerable tool.

Preferably, the body of the LM guide, either articulated or fixed is a one-piece element, e.g. is formed by moulding or machining as one piece, avoiding the assembly of a plurality of elements.

The body is provided with an arrangement of two or more, e.g. 2, 3, 4, 5 channels. The number of channels can depend on the size of the instrument; 18 to 40 channels or more is foreseen. A channel comprises a void space in the body of articulated LM guide. A channel passes from the distal side to the proximal side of the body. A channel preferably has a central axis from the distal side to the proximal side of the body that is parallel to the central axis of the LM guide. A channel can accommodate one, two, or more LMs, preferably only one LM. A channel acts as a constraining point. A channel is dimensioned to constrain the LM, in particular to prevent radial movement with respect to the central axis of the body. A channel is dimensioned to constrain the LM, in particular to prevent axial rotation, i.e. about the LM central (z) axis. Each channel is further configured to maintain the LM at an essentially constant circumferential position on the fictive tube. A channel is dimensioned to facilitate longitudinal slidable movement of the LM therethrough. The channels may be arranged around a fictive tube. Said fictive tube corresponds with the fictive tube of the MTS. The channels are mutually spatially separated. A channel may contain a transverse profile that complements the profile of the LM to be accommodated. A transverse profile is perpendicular to the central axis of the channel. For instance, where the LM has a rectangular profile, the channel may contain a rectangular profile. It is appreciated that the channel profile need not precisely mirror the profile of the LM, for instance a race-track LM profile may be engaged by a rectangular channel.

The plurality of LM guides are tandemly arranged i.e. distal side of one LM guide faces the proximal side of an adjacent LM guide. An example of tandemly-arranged articulated LM guides is shown in FIG. 20. The tandem arrangement of articulated LM guides serve to constrain the LMs at a number of discrete constraining positions along the longitudinal axis of the fictive tube of the MTS. There may be 2 or more (e.g. 3, 4, 5, 6, 7, 8, 9 or 10 or more) tandemly-arranged articulated LM guides providing 2 or more (e.g. 3, 4, 5, 6, 7, 8, 9 or 10 or more) discrete constraining points. Preferably there are 7 or more tandemly-arranged articulated LM guides providing 7 or more discrete constraining points.

The plurality of articulated LM guides are mutually (pairwise) articulated. Preferably, the plurality of articulated LM guides are in mutual (pairwise) contact. It is preferred that the relative rotation of adjacent articulated LM guides (i.e. yawing or axial rotation between adjacent articulated LM guides) is prevented or limited. Prevention or limiting of yawing allows the discrete constraining points to be in essentially fixed mutual rotational alignment along the fictive tube. According to one aspect, a radial line intersecting a discrete constraining point (e.g. a channel) of one articulated LM guide shows a deviation angle, epsilon, of no more than 10 deg, preferably 5 deg compared with that of an adjacent articulated LM guide (see FIG. 23). The radial line radiates from and is perpendicular to the central longitudinal axis (A-A') of the fictive tube. Between adjacent LM guides the point of intersection with the discrete constraining point (e.g. a channel) is the same to enable a comparison.

Preferably, an articulated LM guide contacts an adjacent (neighbouring) LM guide using a pivot joint, such as a ball-and-socket type joint. There may be one ball-and-socket type joint per pair of articulated LM guide. The pivot joint allows pivoting of an articulated LM guide with respect to an adjacent articulated LM guide. The pivot joint may allow two degrees of freedom of movement with respect to an adjacent articulated LM guide i.e. roll and pitch. The pivot joint may allow some relative rotation of adjacent articulated LM guides (i.e. yawing or axial rotation between adjacent articulated LM guides). Prevention or limiting of yawing is preferred but is not necessarily a requirement in view that the use of LMs having an anisotropic area moment of inertia prevents the rotational slack as mentioned earlier, however, it is also within the scope of the invention. It is preferred that the pivot joint may not allow relative rotation of adjacent articulated LM guides (i.e. yawing or axial rotation between adjacent articulated LM guides). Prevention or limiting of yawing can be achieved for instance, using a rotation limiter that might be a protrusion fixed on the body of one articulated LM guide that is received by a recess fixed on the body of an adjacent articulated LM guide (as shown, for instance, in FIG. 18); coupling prevents axial rotation of one LM guide relative to the adjacent LM guide.

A plurality of fixed LM guides are mutually (pairwise) in fixed relation. They are preferably in fixed rotational relation. They are preferably in fixed distance relation. Preferably, the plurality of fixed LM guides are in mutual (pairwise) contact. A plurality of fixed LM guides is configured to reduce the flexibility of TSR compared with the flexibility of the TBDP.

As with adjacent articulated LM guides, relative rotation of adjacent fixed LM guides (i.e. yawing or axial rotation between adjacent fixed LM guides) is prevented. Prevention of yawing allows the discrete constraining points to be in essentially fixed mutual rotational alignment along the fictive tube.

The plurality of LM guides are tandemly arranged such the circularly-arranged channels are in alignment, and each can receive one (or optionally two or more) LMs.

Preferably, the articulated LM guide is substantially disc-shaped, is provided with 10-20 channels each configured to accommodate only one LM, each channel containing a rectangular profile, the long side of the rectangle oriented to face a central axis of the LM guide, the channels being arranged around a fictive circle.

Preferably, the fixed LM guide is substantially cylindrically-shaped, is provided with 10-20 channels each configured to accommodate only one LM, each channel containing a rectangular profile, the long side of the rectangle oriented to face a central axis of the LM guide, the channels being arranged around a fictive circle.

Each channel is configured to constrain the LM to reduce or prevent axial rotation, and to maintain its radial position with respect to a central LM guide axis (A-A').

The MTS may be provided with an end effector, and configured such that the end effector is rotationally fixed in relation to the LMBDP, and the end effector is rotatable when the LMBDP is in a bent position, by a complementary rotation of the LMBPP. Hence, the steerable tool may be configured such that the end effector is rotationally fixed in relation to the BDP and the end effector is rotatable when the BDP is in a bent position, by a complementary rotation of the BPP. The rotationally fixed effector end may be realised by a permanent attachment to the tip of the LMBDP or BDP, for instance be welding or adhesive. Alternatively, the rotationally fixed end effector may be realised by a lockable revolute attachment to the tip of the LMBDP or BDP, in which the end effector is rotationally fixed in relation when the end effector is locked in position.

Reference is made in the description below to the drawings which exemplify particular embodiments of the invention; they are not at all intended to be limiting. It will be understood that the skilled person may adapt the device and substitute components and features according to the common practices of the skilled artisan.

FIG. 1 depicts a mechanical transmission system (MTS) of the invention 100 shown in isolation having a proximal end 20 and a distal end 40, and a central longitudinal axis A-A'. The MTS 100 comprising a plurality (i.e. 4) of longitudinal members (LMs) 110 arranged longitudinally and dispersed evenly around a fictive longitudinal tube 120 having a cylindrical shape. The MTS 110 contains a transmission bendable distal part (TBDP) 130 and a transmission shaft region (TSR) 132 that is essentially rigid or semi-rigid in the shaft region of the steerable tool, or that is maintained rigid or semi-rigid in the shaft region of the steerable tool by co-operating with an exotube.

Figure 2:
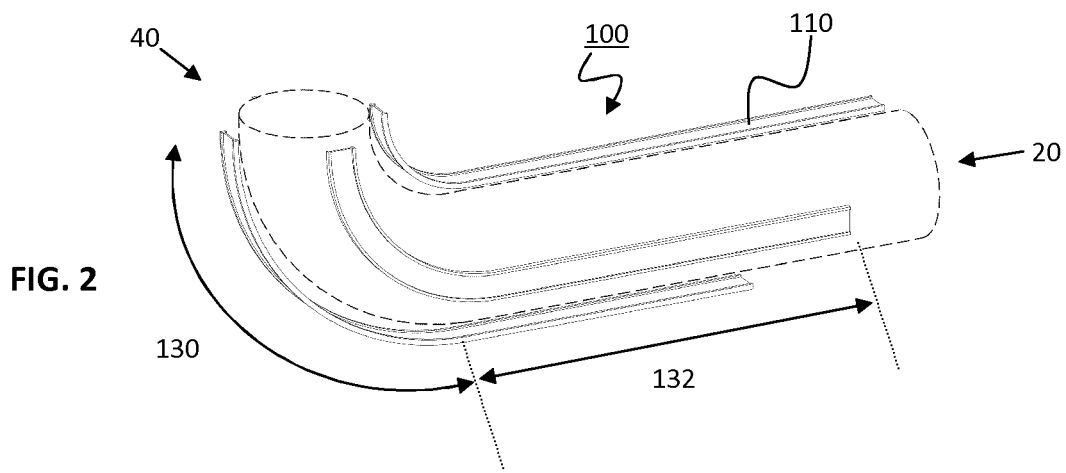
FIG. 2 depicts the MTS of FIG. 1 in which the transmission bendable distal part (TBDP) is bent, and the transmission shaft region (TSR) remains in the same straight configuration.

FIG. 2 depicts the MTS 100 of FIG. 1 in which the TBDP 130 is bent, and the TSR 132 remains in the same straight configuration.

FIG. 3 depicts two intersecting axes 116 (x-axis), 118 (y-axis) on a plane section 114 that is a planar transverse cross-section of the LM 110 at position 112 in FIG. 1, which cross-section has an "I"-shaped profile. The axes intersect at a point 111 that is a centroid of the profile (outer shape) of the planar transverse cross-section 114. The axes 116, 118 are mutually perpendicular. The axis 116 around which the LM has the higher area moment of inertia (x-axis, 116) is oriented such that it is essentially radial to the central (A-A') axis of the MTS. A z-axis 119 is also indicated that is perpendicular to both the x-axis 116, y-axis 118.

Figure 4:
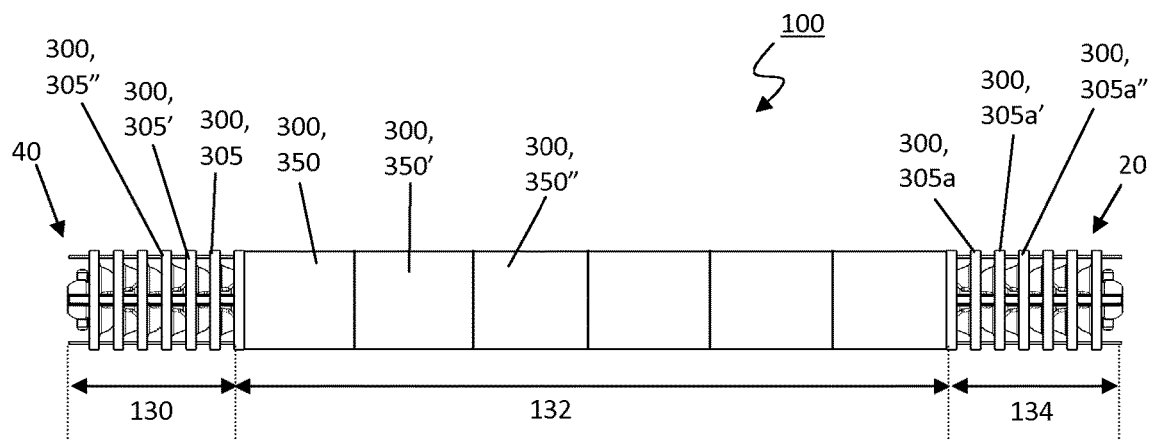
FIG. 4 depicts an outer view of an MTS of the invention disposed with a plurality of fixed LM guides and a plurality of articulated LM guides.

FIG. 4 depicts an outer view of an MTS 100 of the invention, having a proximal 20 and distal end 40, and transmission bendable distal part (TBDP) 130, a transmission shaft region (TSR) 132 and a transmission bendable proximal part (TBPP) 134. The transmission shaft region (TSR) 132 is disposed with a plurality of fixed LM guides 350, 350', 350" each providing constraining points for axial rotational of the LM wherein each LM is longitudinally slidable with respect to each LM guide 350, 350', 350". The TBDP 130 and TBPP 134 are disposed with a plurality of articulated LM guides 305, 305', 305", 305a, 305a', 305a" each providing a discrete constraining point for axial rotational of the LM wherein each LM is longitudinally slidable with respect to each LM guide 305, 305', 305", 305a, 305a', 305a".

Figure 5:
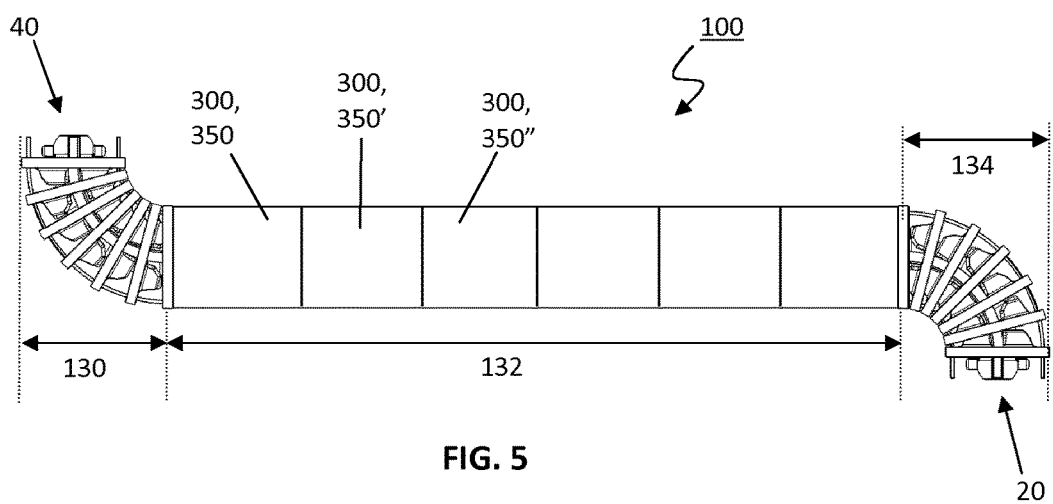
FIG. 5 depicts the MTS of FIG. 4, in which TBPP has been actuated by bending, the movement transmitted to the TBDP.

FIG. 5 depicts the MTS 100 of FIG. 4, in which TBPP 134 has been actuated by bending, the movement transmitted to the TBDP 130 along the TSR 132 by the MTS, which TBDP 130 bends responsively.

Figures 6, 7, 8, 9, 10:
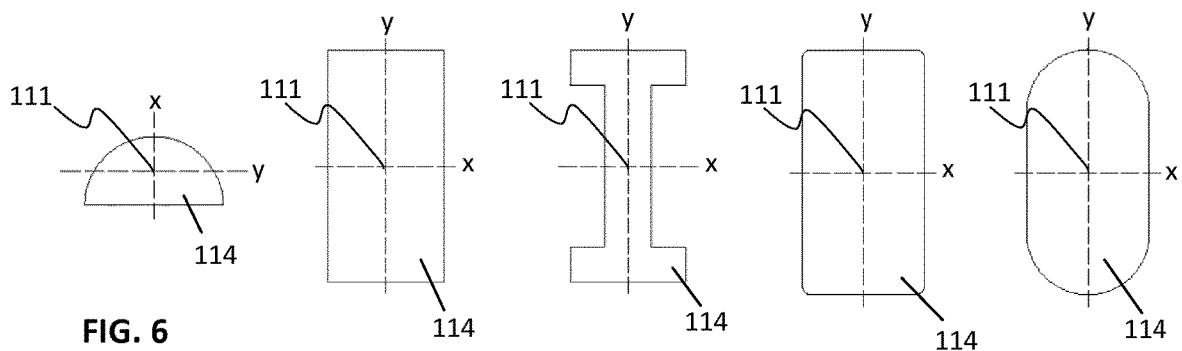
FIG. 6 depicts a semi-circular transverse cross-section (i.e. plane section) of an LM.
FIG. 7 depicts a rectangular transverse cross-section (i.e. plane section) of an LM.
FIG. 8 depicts an "I" transverse cross-section (i.e. plane section) of an LM.
FIG. 9 depicts a rounded-edged rectangular transverse cross-section (i.e. plane section) of an LM.
FIG. 10 depicts a race-track transverse cross-section (i.e. plane section) of an LM.

FIG. 6 depicts a semi-circular transverse cross-section (i.e. plane section 114) of an LM, and intersecting x- and y-axes about which moments of inertia are measured, which axes are centred at point 111 that is the centroid of the cross-section. The ratio $I_x/I_y$=3.57, which is calculated according to Eq 1 and Eq 2.

FIG. 7 depicts a rectangular transverse cross-section (i.e. plane section 114) of an LM, and intersecting x- and y-axes about which moments of inertia are measured, which axes are centred at point 111 that is the centroid of the cross-section. The ratio $I_x/I_y$=4, which is calculated according to Eq 1 and Eq 2.

FIG. 8 depicts an "I" transverse cross-section (i.e. plane section 114) of an LM, and intersecting x- and y-axes about which moments of inertia are measured, which axes are centred at point 111 that is the centroid of the cross-section. The ratio $I_x/I_y=9.2$, which is calculated according to Eq 1 and Eq 2.

FIG. 9 depicts a rounded-edged rectangular transverse cross-section (i.e. plane section 114) of an LM, and intersecting x- and y-axes about which moments of inertia are measured, which axes are centred at point 111 that is the centroid of the cross-section. The ratio $I_x/I_y=4$, which is calculated according to Eq 1 and Eq 2.

FIG. 10 depicts a race-track transverse cross-section (i.e. plane section 114) of an LM, and intersecting x- and y-axes about which moments of inertia are measured, which axes are centred at point 111 that is the centroid of the cross-section. The ratio $I_x/I_y=4$, which is calculated according to Eq 1 and Eq 2.

Figure 11:
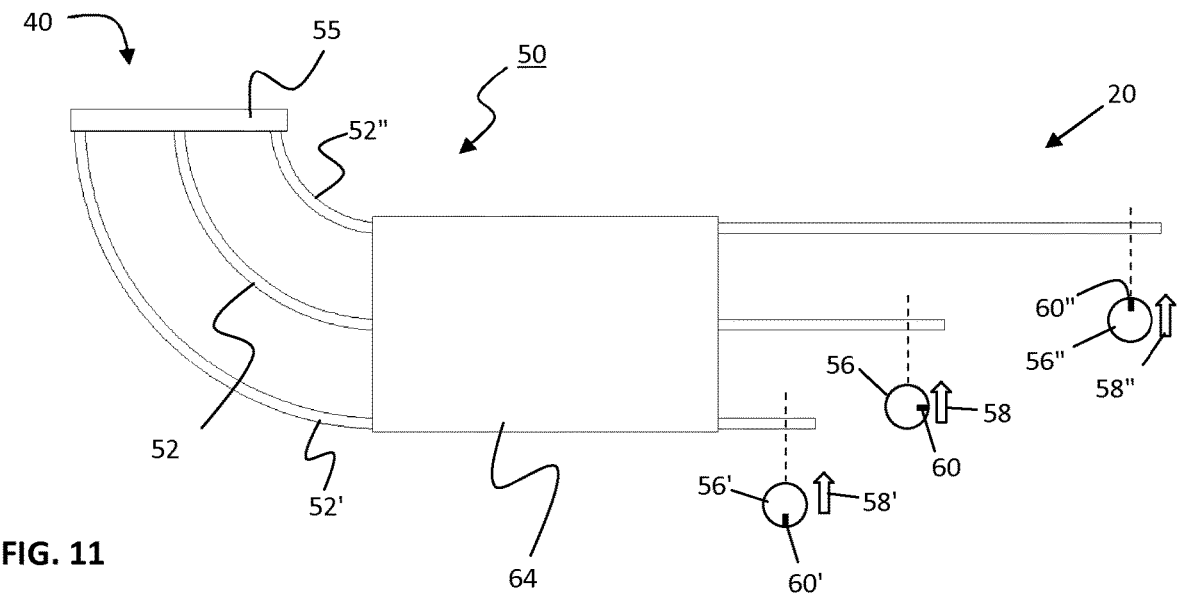
FIG. 11 depicts a side view of a mechanical transmission means, not of the invention, in which the longitudinal members each have a circular plane sections.

FIG. 11 depicts a side view of a mechanical transmission means 50, not of the invention, having a proximal end 20 and a distal 40 end, and formed using longitudinal members 52, 52', 52" connected at the distal end to a distal longitudinal members fixation element 55. The transmission shaft region is provided with a fixed longitudinal member guide 64. Transverse cross-sections of the longitudinal members 52, 52', 52" are each depicted having a circular plane sections 56, 56', 56". Bending of each of the longitudinal members 52, 52', 52" is apparently facilitated by the circularly-profiled longitudinal members having an isotropic area moment of inertia, particularly in respect of those longitudinal members e.g. 52 that are peripheral to the longitudinal members 52', 52" actuating the bending movement. Hence, all the longitudinal members 52, 52', 52" bend with equal resistance, despite each longitudinal member e.g. 52, 52', 52" bending in a different relative direction (see direction of arrow 58, 58', 58", compared with an orientation marker 60, 60', 60").

FIG. 12 depicts a side view of a MTS 100 of the invention, having a proximal end 20 and a distal 40 end, and formed using LMs 110, 110, 110" connected at the distal end to a distal LM fixation element 113. The transmission shaft region (TSR) is provided with a fixed LM guide 350. Plane sections 114, 114', 114" of the LM 110, 110, 110" are depicted with "I"-shaped profiles. Bending of each of the LM 110, 110, 110" is surprisingly not hindered by the "I"-shaped-profiled LMs having plane sections with an anisotropic area moment of inertia, particularly in respect of those LMs e.g. 110 that are peripheral to the longitudinal members 110', 110" actuating the bending movement. Hence, all the longitudinal members 110, 110', 110" bend without buckling or twisting, despite each longitudinal member e.g. 110, 110', 110" bending in a different relative direction (see direction of arrow 158, 158', 158"), and despite the peripheral longitudinal members e.g. 110, bending in a direction that has a greater area moment of inertia.

Figure 13:
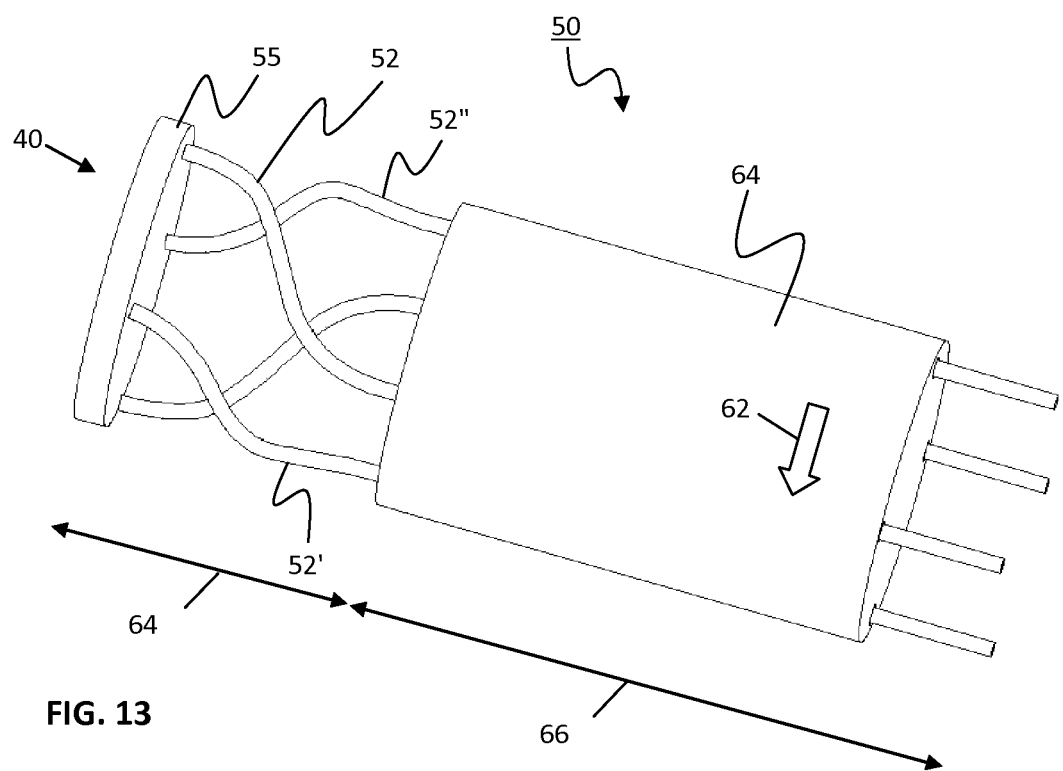
FIG. 13 is an isometric view of a mechanical transmission means not of the invention, in which the longitudinal members each have a circular plane sections, demonstrating the undesirable twisting of longitudinal members.

FIG. 13 is a schematic view of a mechanical transmission means 50 of FIG. 11 and not of the invention, demonstrating the twisting of longitudinal members 52, 52', 52" in a distal bendable part 64 when torque 62 is applied to a shaft region 66. Each of the longitudinal members 52, 52', 52" has a circular profile and thus an isotropic area moment of inertia. Hence, the use of circular longitudinal members introduces a backlash in the transmission of torque through the shaft region 66 and to the bendable distal part 64.

Figure 14:
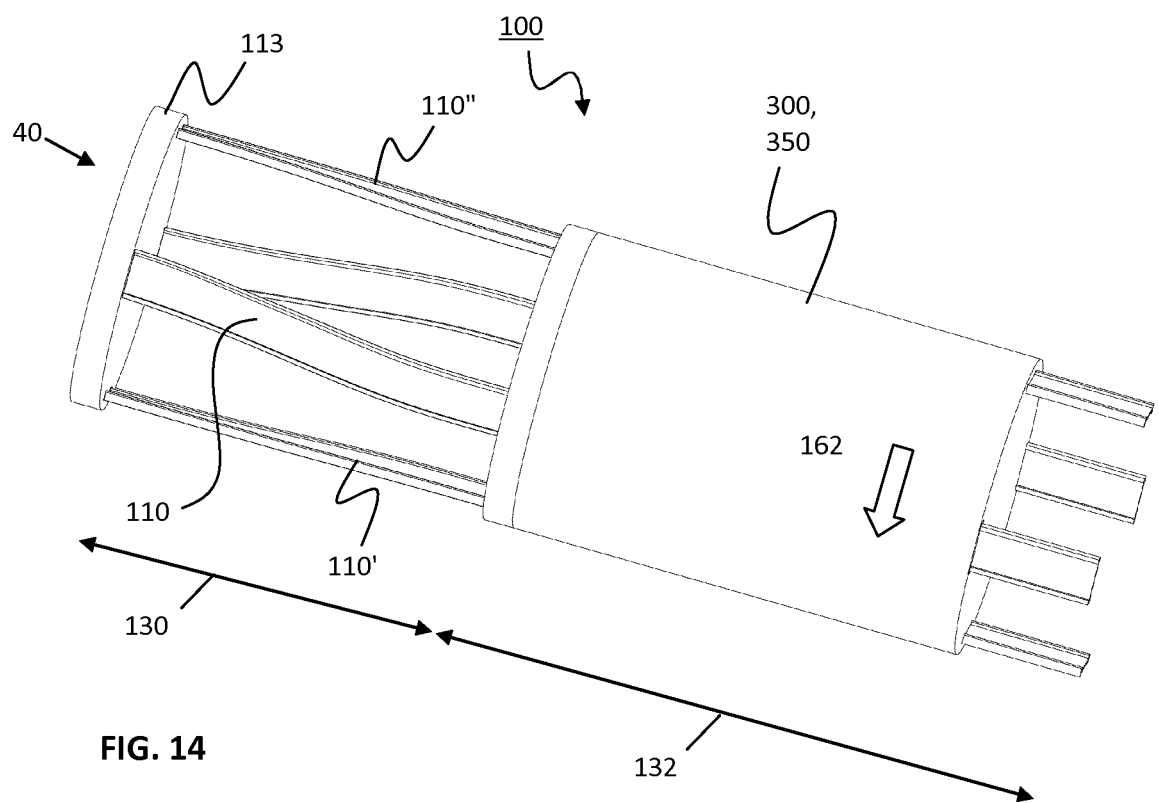
FIG. 14 is an isometric view of a MTS of FIG. 11 and of the invention, in which the LM each have an "I"-shaped plane section demonstrating a significantly lesser twisting of LMs in the TBDP.

FIG. 14 is a schematic view of a MTS 100 of FIG. 11 and of the invention, demonstrating a significantly lesser twisting of LMs 110, 110', 110" in the transmission bendable distal part (TBDP) 130 when torque 162 is applied to the TSR 132. Each of the longitudinal members 110, 110', 110" has an "I"-shaped plane section, and thus an anisotropic area moment of inertia. Hence, the use of "I"-profiled LMs reduces or removes backlash in the transmission of torque through the LM shaft region 132 and to the TBDP 130.

Figure 15:
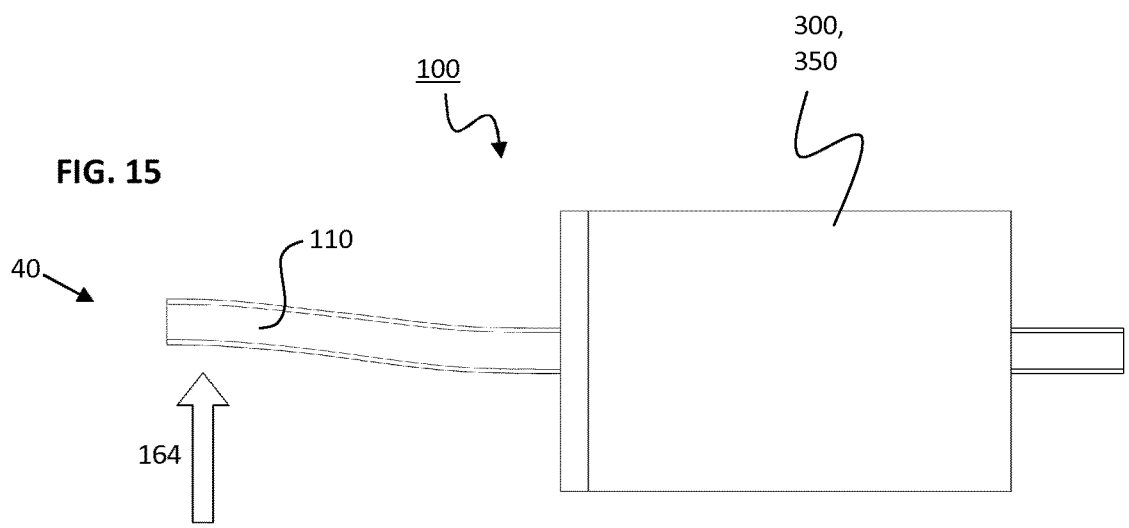
FIG. 15 is a side view of an MTS of FIG. 14 and of the invention, showing an isolated single LM.

FIG. 15 is a schematic view of an MTS 100 of FIG. 14 and of the invention, showing an isolated single LM 110. It shows the application of force (164) to the LM 110 and its resistance to bending, attributable to the anisotropic area moment of inertia.

Figure 16:
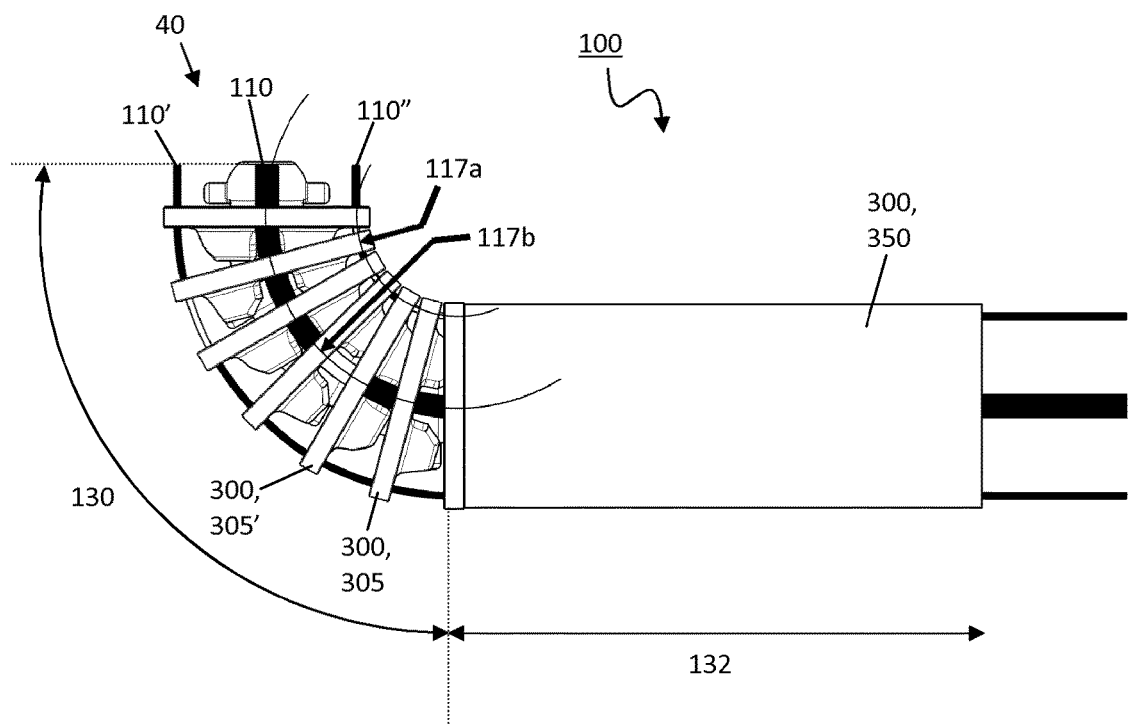
FIG. 16 is a side view of an MTS showing different bending radii of LMs disposed in the TBDP of the MTS.

FIG. 16 shows the different bending radii of anterior 110", posterior 110' and lateral 110 LMs disposed in the MTS 100 in the TBDP 130. The bending radius 117a is smaller for the anterior LM 110" located on the inside the bend, compared with the bending radius 117b of the lateral LM 110, which lateral LM 110 is stiffer in the bending direction owing to the anisotropic area moment of inertia of the LM 110.

Figure 17:
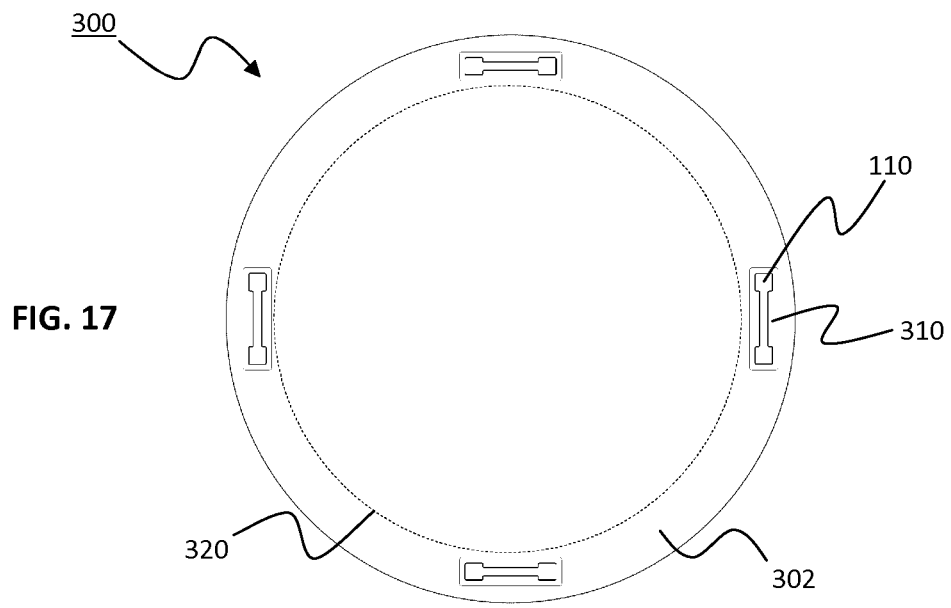
FIG. 17 is a plan view of an LM guide that is disc shaped.

FIG. 17 is a plan view of an LM guide 300 that is disc shaped. The LM guide 300 has a body 302 is disposed with 4 separate channels 310, arranged around a fictive tube 320. The fictive tube 320 corresponds with the fictive tube 120 in FIG. 1. Each channel 310 constrains a LM 110. Each channel is regarded as a discrete constraining point.

Figure 19:
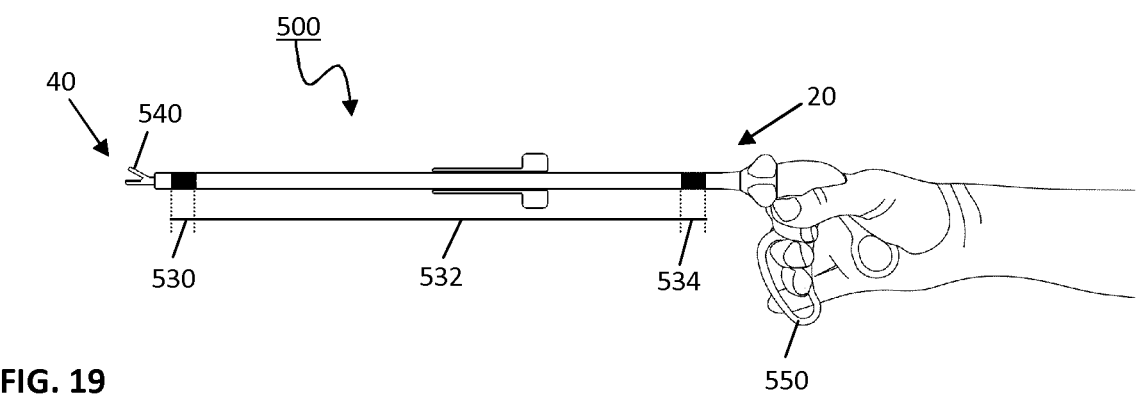
FIG. 19 shows an isometric view of a steerable tool incorporating an MTS of the invention.

FIG. 18 is a side view of a LM guide 300 that is an articulated LM guide 305 having a disc shaped, and a distal side 40 and a proximal side 20. The articulated LM guide 300 has a body 302 comprising at the distal side 40, one component of the pair of components that forms a pivot joint that is a dome protrusion 330, akin to the ball of a ball and socket joint. It further comprises at the proximal side 20, the other component of the pair of components that forms a pivot joint that is a reciprocating recess 340, akin to the socket of a ball and socket joint. Further indicated is a pair of rotation limiters (332, 332') fixedly connected to the dome protrusion 330, which are radial protrusions from said dome protrusion 330. These couple with a pair reciprocating slots 340, 340' fixedly connected to the receiving recess 340 of an adjacent articulated LM guide (not shown), to prevent mutual axial rotation of adjacent articulated LM guides. Each articulated LM guide contains a discrete constraining point (i.e. a channel) and the pair of rotation limiters provide an essentially fixed mutual rotational alignment of the discrete constraining point along the fictive tube. FIG. 19 shows a steerable tool 500 incorporating an MTS of the invention. The steerable tool 500 has a proximal 20 and distal 40 end. The distal end 40 is provided with an end effector (540) that is a gripper, while the proximal end 20 is provided with a handle 550 to steer the tube and to control the gripper. Also indicated are the bendable distal part (BDP) 530, the shaft region (SR) 532 and the bendable proximal part (BPP) 534.

FIG. 20 is schematic view of a MTS 100 of the invention having a proximal end 20 and a distal end 40, provided with 4 LMs 110 arranged around a fictive tube, maintained in position with a plurality of articulated LM guides 305, 305', 305" in the TBDP 130 each provided with a plurality of aligned channels. One of a complementary pair of elements (domed protrusion 330) of a pivot joint is indicated in the distal most LM guide 300". The TSR 132 contains a plurality of tandemly-arranged fixed LM guide 350, 350', 350" that maintain the position of the LMs 110 in the TSR 130.

FIG. 21A shows a bendable distal part of a mechanical transmission means 50, not of the invention, having a proximal 20 and distal end 40. The mechanical transmission means 50 is disposed with circularly-profiled longitudinal members 52, 52', 52" each having an isotopic second area moment of inertia, which longitudinal members 52, 52', 52" are constrained in a radial and circumferential position by a plurality of articulated longitudinal member guides 54, 54', 54". Adjacent articulated longitudinal member guides 54, 54', 54" are prevented from mutual axial rotation due to the presence of rotation limiters (not indicated) on each longitudinal member guide 54, 54', 54".

FIG. 21B shows the bendable distal part of a mechanical transmission means 50 of FIG. 21A and not of the invention, that has entered the undesirable and stable spiral kinematic chain state whereby the circularly-profiled longitudinal members 52, 52', 52" at the proximal end 20 are twisted relative to the distal end 40 despite the presence of rotation limiters.

FIG. 22 shows two exemplary orientations of a longitudinal member 110a, 110b present in an LM guide channel 310 or 310' wherein the x-axis of a plane section 114 of one longitudinal member 110b is shown to diverge from an imaginary line 115 draw between the central (A-A') axis and the centroid 111 of the plane section 114 by angle alpha when constrained by LM guide channel 310'. The other longitudinal member 110a shows no such divergence i.e. alpha is zero when constrained by LM guide channel 310.

FIGS. 22A and 22B illustrate an angle beta that is a change in an axial rotational angle of an LM 110. FIG. 22A represents a starting orientation of an axis (x), and FIG. 22B represent the axis (x') at one of the limits of rotation within a channel 310. For an essentially constant axial rotational angle of an LM 110 i.e. where the LM is axially rotationally constrained at a discrete constraining point, angle beta deviates between certain limits.

FIGS. 23 I and II illustrate a TDBP (130) disposed with a plurality of articulated LM guides (305B to E) and a central longitudinal axis (A-A') of the fictive tube and a TSR (132) disposed with a fixed LM guides (305A). In I, the TDBP (130) is straight (unactuated), and in II, the TDBP (130) is curved (actuated). FIGS. 23 Y and X show schematic plan views of separate LM guides to illustrate the deviation angle, epsilon. FIG. 23A shows the radial line (312X) of one LM guide (305X) projecting from the central longitudinal axis (A-A') of the fictive tube and intersecting its channel 310X, FIG. 23Y shows the radial line (312Y) of another LM guide (305X) intersecting its channel 310X. X and Y are the LM guides between which epsilon is to be measured. For instance, where epsilon is a measure of deviation angle between two adjacent articulated LM guides, X may be I-C and Y may be I-D. Where epsilon is a measure of deviation angle between a proximal-most articulated LM-guide and a distal-most articulated LM-guide in the TBDP (130), X may be I-B and Y may be I-E. Where epsilon is a measure of deviation angle between the fixed LM guide in the TSR (132) and a distal-most articulated LM-guide, X may be I-A and Y may be I-E.

The angular difference between the radial lines (312A and 312X) of these respective LM guides, the deviation angle, is indicated as epsilon. FIGS. 23 I-A to I-E are schematic plan views of the separate LM guides of FIG. 23 wherein there is no deviation (epsilon is zero) between adjacent LM guides, and when the TDBP (130) is straight (unactuated). FIGS. 23 II-A to II-E are schematic plan views of the separate LM guides of FIG. 23-II wherein there is no deviation (epsilon is zero) between adjacent LM guides, and when the TDBP (130) is curved (bend).

The invention claimed is:

1. A steerable tool comprising:
a mechanical transmission system comprising:
at least four longitudinal members each having a proximal and distal end, arranged in a longitudinal direction around a geometric shape that is a tube,
a transmission shaft region, transmission bendable proximal part that is omnidirectionally moveable and bendable along a curve, and transmission bendable distal part that is omnidirectionally moveable and bendable along a curve,
wherein the longitudinal members transmit longitudinal forces to bend the transmission bendable distal part responsive to movement of the transmission bendable proximal part,
wherein a plane section of at least one longitudinal member has an anisotropic area moment of inertia,
wherein a majority of the longitudinal members are each constrained at one or more constraining points along the transmission bendable distal part or along the transmission shaft region,
wherein, at the constraining point, rotation around a longitudinal axis of the longitudinal member is constrained,
wherein the longitudinal members are longitudinally slidable with respect to each discrete constraining point, and
wherein the mechanical transmission system is configured such that a transmission bendable distal part tip is axially rotatable in a bent position by a complementary rotation of the transmission bendable proximal part.

2. The steerable tool according to claim 1, wherein said majority of the longitudinal members are each further axially rotationally constrained at one or more constraining points along the transmission bendable proximal part.

3. The steerable tool according to claim 1, provided with at least two longitudinal member guides in the transmission bendable distal part and at least two longitudinal member guides in the transmission bendable proximal part.

4. The steerable tool according to claim 1, wherein the plane section of the longitudinal member has a rectangular, letter "I", or circular segment profile.

5. The steerable tool according to claim 1, wherein the plane section of the longitudinal member has a rectangular, letter "I", or circular segment profile, wherein one or more profile corners are pointed or rounded-off.

6. The steerable tool according to claim 1, wherein the at least one constraining point disposed along the transmission shaft region is provided in the distal half of the transmission shaft region, and at least one other constraining point disposed along the transmission shaft region is provided in the proximal half of the transmission shaft region.

7. The steerable tool according to claim 6, wherein the at least one constraining point disposed along the transmission shaft region is provided in 10% of the transmission shaft region total length located at a distal end of the transmission shaft region and at least one other constraining point disposed along the transmission shaft region is provided in 10% of the transmission shaft region total length located at a proximal end of the transmission shaft region.

8. The steerable tool according to claim 1, wherein the transmission shaft region is flexible.

9. The steerable tool according to claim 8, wherein the transmission shaft region is configured to become rigid or semi-rigid when co-operating with a rigid or semi-rigid exotube or outer tube.

10. The steerable tool according to claim 1, further provided with one or more longitudinal member guides each configured to axially rotationally constrain said majority of the longitudinal members at the constraining points.

11. The steerable tool according to claim 10, wherein each of the longitudinal member guides is further configured to maintain said majority of the longitudinal members at constant circumferential positions on the geometric shape that is the tube at the constraining points.

12. The steerable tool according to claim 10, wherein the longitudinal member guides in the transmission shaft region are fixed longitudinal member guides and are rotationally fixed with respect to each other to reduce the flexibility of the transmission shaft region compared with the flexibility of the transmission bendable distal part or the transmission bendable proximal part.

13. The steerable tool according to claim 10, wherein the longitudinal member guide comprises a body provided with a plurality of discrete channels arranged around the geometric shape that is the tube configured to axially rotationally constrain said majority of the longitudinal members at the constraining point, and to maintain the longitudinal members at a constant circumferential position on the geometric shape that is the tube at the constraining point.

14. The steerable tool according to claim 13, wherein a channel configured to axially rotationally constrain a longitudinal member in the transmission bendable distal part or transmission bendable proximal part contains a profile in transverse cross-section that complements the plane section of the longitudinal member.

15. The steerable tool according to claim 10, wherein the longitudinal member guides in the transmission bendable distal part and transmission bendable proximal part are articulated longitudinal member guides respectively tandemly arranged, and mutually articulated, thereby supporting bending of the longitudinal members in the transmission bendable distal part and transmission bendable proximal part respectively.

16. The steerable tool according to claim 15, wherein the articulated longitudinal member guides are in pairwise mutual contact through a pivot joint that comprises a ball and socket joint.

17. The steerable tool according to claim 15, wherein yawing between adjacent articulated longitudinal member guides is limited to provide a fixed mutual rotational alignment of the discrete constraining points along the geometric shape that is the tube.

* * * * *